United States Patent
Chandak et al.

(10) Patent No.: US 12,372,565 B2
(45) Date of Patent: Jul. 29, 2025

(54) METHODS AND APPARATUS FOR DETERMINING PARASITIC CAPACITANCES

(71) Applicant: Texas Instruments Incorporated, Dallas, TX (US)

(72) Inventors: Aatish Chandak, Bengaluru (IN); Aravind Miriyala, Bengaluru (IN); Midhun Raveendran, Bengaluru (IN); Anand Hariraj Udupa, Bengaluru (IN); Raja Reddy Patukuri, Bengaluru (IN); Prabin Krishna Yadav, Bengaluru (IN)

(73) Assignee: Texas Instruments Incorporated, Dallas, TX (US)

( * ) Notice: Subject to any disclaimer, the term of this patent is extended or adjusted under 35 U.S.C. 154(b) by 155 days.

(21) Appl. No.: 18/128,912

(22) Filed: Mar. 30, 2023

(65) Prior Publication Data
US 2024/0027508 A1    Jan. 25, 2024

(30) Foreign Application Priority Data
Jul. 12, 2022   (IN) .............................. 202241039856

(51) Int. Cl.
*G01R 27/28*     (2006.01)
*A61B 5/053*     (2021.01)
*G01R 31/00*     (2006.01)

(52) U.S. Cl.
CPC ............ *G01R 31/002* (2013.01); *A61B 5/053* (2013.01); *A61B 2560/0223* (2013.01)

(58) Field of Classification Search
CPC ..... G01R 31/002; G01R 29/00; G01N 27/028
See application file for complete search history.

(56) References Cited

U.S. PATENT DOCUMENTS

| | | | |
|---|---|---|---|
| 2006/0087339 A1* | 4/2006 | Chung | H04L 25/0278 326/30 |
| 2008/0001608 A1* | 1/2008 | Saulnier | A61B 5/0536 324/601 |
| 2011/0234201 A1* | 9/2011 | Tanaka | H01J 37/32935 324/76.39 |
| 2019/0008042 A1* | 1/2019 | Akiyama | H05K 3/46 |
| 2021/0003523 A1 | 1/2021 | Chandak et al. | |
| 2021/0330212 A1* | 10/2021 | Ganesan | A61B 5/7225 |
| 2021/0375798 A1* | 12/2021 | Ma | H01L 23/645 |
| 2022/0178980 A1* | 6/2022 | Lee | G01R 17/02 |

* cited by examiner

*Primary Examiner* — Thang X Le
(74) *Attorney, Agent, or Firm* — John R. Pessetto; Frank D. Cimino

(57) ABSTRACT

An example apparatus includes: calibration circuitry configured to determine a second current at a second terminal of a second impedance circuit based on a first parasitic capacitance, a first impedance value, a third impedance value, a first voltage, and a second voltage; determine a third voltage at a second terminal of a second impedance circuit based on the first parasitic capacitance, a second impedance value, the third impedance value, the second voltage, and the second current; and determine a second parasitic capacitance between the second terminal of the second impedance circuit and the second terminal of a fifth impedance circuit based on the second current, the third voltage, a third current at the second terminal of the fifth impedance circuit, and a fourth voltage at the second terminal of the fifth impedance circuit.

7 Claims, 12 Drawing Sheets

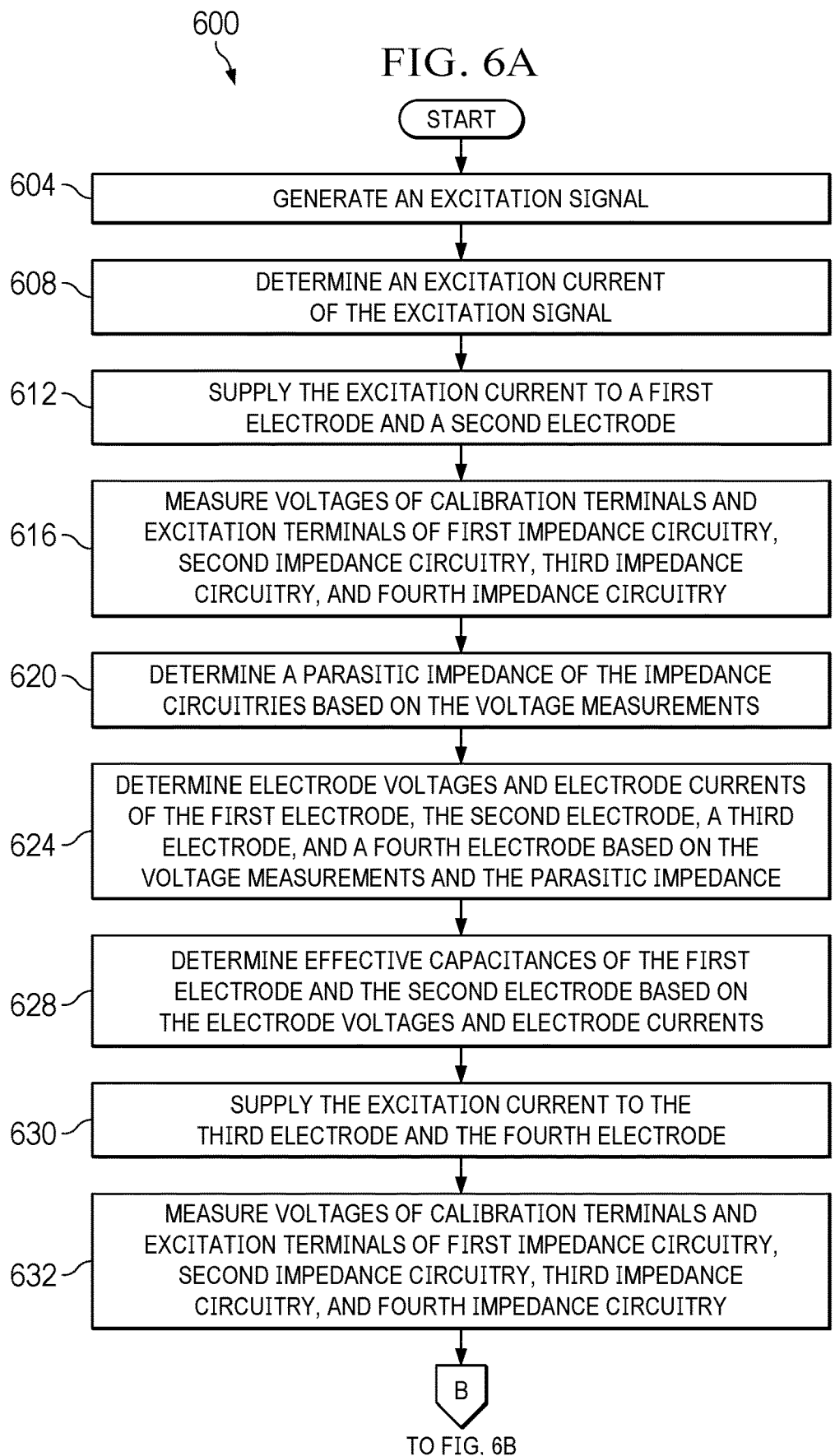

METHODS AND APPARATUS FOR DETERMINING PARASITIC CAPACITANCES

CROSS-REFERENCE TO RELATED APPLICATION

This patent application claims the benefit of and priority to IN Provisional Patent Application No. 202241039856 filed Jul. 12, 2022, which application is hereby incorporated herein by reference in its entirety.

TECHNICAL FIELD

This description relates generally to capacitors, and more particularly to methods and apparatus for determining parasitic capacitances.

BACKGROUND

Continuing advancements in electronics allow for system on chip (SoC) sizes of circuitry to continuously decrease. In some devices, such as wearable devices, increasingly complex circuitry is often constrained by decreasing package sizes. As circuitry becomes increasingly compact, additional considerations of electrical characteristics resulting from reducing SoC sizes need to occur during design, development, and testing. One such design consideration is creation of parasitic capacitances, capable of substantively effecting electrical characteristics of circuitry. One source of parasitic capacitances is placing electrical components and/or electrical traces in a relatively close proximity to one another. Such parasitic capacitances result from components and/or traces acting as plates and spacing between them acting as a dielectric region. To prevent parasitic capacitances from affecting circuitry, designers typically distance components and/or traces to increase the dielectric region, which reduces the parasitic capacitance.

SUMMARY

For methods and apparatus for determining parasitic capacitances, an example apparatus includes: first impedance circuitry including: a first impedance circuit having a first terminal, a second terminal, and a first impedance value; a second impedance circuit having a first terminal, a second terminal, and a second impedance value, the first terminal of the second impedance circuit coupled to the second terminal of the first impedance circuit; and a third impedance circuit having a first terminal, a second terminal, and a third impedance value, the first terminal of the third impedance circuit coupled to the second terminal of the first impedance circuit; second impedance circuitry including: a fourth impedance circuit having a first terminal, a second terminal, and the first impedance value; a fifth impedance circuit having a first terminal, a second terminal, and the second impedance value, the first terminal of the fifth impedance circuit coupled to the second terminal of the fourth impedance; and a sixth impedance circuit having a first terminal, a second terminal, and the third impedance value, the first terminal of the sixth impedance circuit coupled to the second terminal of the fourth impedance circuit; and calibration circuitry coupled to the first impedance circuitry and the second impedance circuitry, the calibration circuitry configured to: determine a first parasitic capacitance based on a first current at the first terminal of the first impedance circuit, the first impedance value, the third impedance value, a first voltage at the first terminal of the first impedance circuit, and a second voltage at the second terminal of the third impedance circuit; determine a second current at the second terminal of the second impedance circuit based on the first parasitic capacitance, the first impedance value, the third impedance value, the first voltage, and the second voltage; determine a third voltage at the second terminal of the second impedance circuit based on the first parasitic capacitance, the second impedance value, the third impedance value, the second voltage, and the second current; and determine a second parasitic capacitance between the second terminal of the second impedance circuit and the second terminal of the fifth impedance circuit based on the second current, the third voltage, a third current at the second terminal of the fifth impedance circuit, and a fourth voltage at the second terminal of the fifth impedance circuit.

BRIEF DESCRIPTION OF THE DRAWINGS

FIGS. 6A, 6B, and 6C are a flowchart representative of an example process that may be performed using machine readable instructions that can be executed and/or performed using another example hardware implementation of the measurement circuitry of FIGS. 1 and 3 to determine the parasitic capacitances of FIG. 2

The same reference numbers or other reference designators are used in the drawings to designate the same or similar (functionally and/or structurally) features.

DETAILED DESCRIPTION

Figure 1:
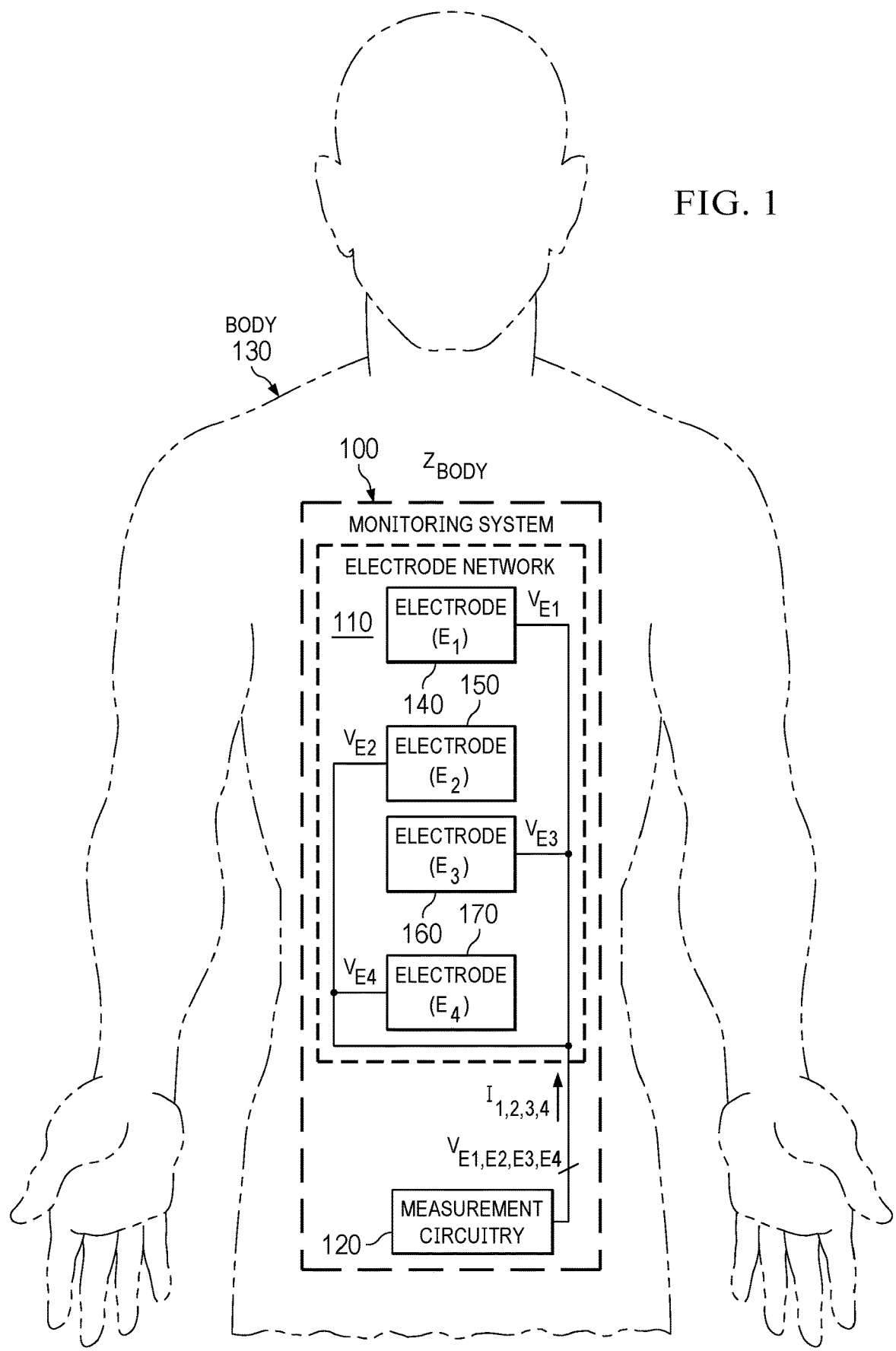
FIG. 1 is a block diagram of an example monitoring system including an example electrode network and example measurement circuitry, in which the monitoring system monitors an impedance of a body.

The drawings are not necessarily to scale. Generally, the same reference numbers in the drawing(s) and this description refer to the same or like parts. Although the drawings show regions with clean lines and boundaries, some or all of these lines and/or boundaries may be idealized. In reality, the boundaries and/or lines may be unobservable, blended and/or irregular.

As system on chip (SoC) sizes of circuitry continue to decrease, designers are capable of decreasing device package sizes. Some applications incentivize decreasing a size of a device package, such as wearable devices. As circuitry becomes increasingly compact, additional considerations of electrical characteristics resulting from reducing SoC size need to occur during design, development, and testing. One such design consideration is creation of parasitic capacitances that can substantively affect electrical characteristics of circuitry. Parasitic capacitances may be formed by placing electrical components and/or electrical traces in a relatively close proximity to one another. Such parasitic capacitances result from components and/or traces acting as plates and spacing between them acting as a dielectric region.

One method of preventing parasitic capacitances from affecting circuitry is to increase spacing between components. Such spacing increases a size of the dielectric region to substantially reduce the parasitic capacitance. In some applications, spacing components to reduce parasitic capacitance substantially increases the SoC size. In other applications, such as measurement systems, increasing spacing between components may substantially modify operations of the circuitry.

Another method of preventing parasitic capacitances from affecting circuitry is adding isolation circuitry to the SoC to account for parasitic capacitances. The isolation circuitry prevents parasitic capacitances from modifying operations of the circuitry. However, such a method of using isolation circuitry increases the SoC size, the device cost, and the circuitry complexity.

Examples described herein include measurement circuitry to determine and account for parasitic capacitances using calibration circuitry. In some described examples, the measurement circuitry includes impedance circuitries to set and measure voltages. The calibration circuitry determines parasitic capacitances of the impedance circuitries and parasitic capacitances between components coupled to the impedance circuitries. In one described example, the calibration circuitry determines parasitic cross capacitances generated by electrodes in a relatively close proximity. The calibration circuitry uses voltages of the impedance circuitries in response to an excitation to determine parasitic capacitances. Advantageously, determining parasitic capacitances allows the measurement circuitry to account for the parasitic capacitances in measurements, which increases an accuracy of the measurements.

FIG. 1 is a block diagram of an example monitoring system 100 including an example electrode network 110 and example measurement circuitry 120. In the example of FIG. 1, the monitoring system 100 is coupled to an example body 130. The monitoring system 100 monitors an impedance ($Z_{BODY}$) of the body 130. Using the impedance of the body 130, the monitoring system 100 may calculate physical properties of the body 130.

The electrode network 110 is coupled to the measurement circuitry 120. In the example of FIG. 1, the electrode network 110 is coupled to the body 130. In the example of FIG. 1, the electrode network 110 includes a first example electrode ($E_1$) 140, a second example electrode ($E_2$) 150, a third example electrode ($E_3$) 160, and a fourth example electrode ($E_4$) 170. Alternatively, the electrode network 110 may be modified in accordance with the teachings described herein to include any plurality of electrodes.

The electrode network 110 receives an excitation signal from the measurement circuitry 120. The electrode network 110 modifies electrode voltages and electrode currents based on the impedance of the body 130 and parasitic capacitances between the electrodes 140-170. The measurement circuitry 120 determines the electrode voltages and the electrode currents of the electrodes 140-170.

The electrodes 140-170 are coupled to the measurement circuitry 120. In the example of FIG. 1, the electrodes 140-170 are coupled to the body 130. In some examples, the measurement circuitry 120 supplies an excitation signal to one or more of the electrodes 140-170. In such examples, the one or more of the electrodes 140-170 supply the excitation signal to the body 130. The excitation signal modifies the electrode voltages of the electrodes 140-170 based on the impedance of the body 130 and parasitic capacitances of the electrode network 110. Examples of the electrodes 140-170 are described below by reference to FIG. 2. Examples of parasitic capacitances of the electrode network 110 are also described below by reference to FIG. 2.

The measurement circuitry 120 is electrically coupled to the electrode network 110. In some examples, the measurement circuitry 120 supplies an excitation signal to one of the electrodes 140-170. In other examples, the measurement circuitry 120 supplies an excitation signal to two of the electrodes 140-170. The measurement circuitry 120 determines the voltages of the electrodes 140-170 in response to the excitation signal. The measurement circuitry 120 determines the parasitic capacitances of the electrode network 110 based on the response of the electrodes 140-170 to the excitation signal. In some examples, the electrode network 110 is removed from (e.g., no longer mechanically coupled to) the body 130 prior to the measurement circuitry 120 determining the parasitic capacitances of the electrode network 110. In such an example, changes in electrode voltages of the electrodes 140-170 result from the parasitic capacitances. An example of the measurement circuitry 120 is described below by reference to FIG. 3. Example operations to determine the parasitic capacitances are described below by reference to FIGS. 4 and 5A-6C.

Figure 2:
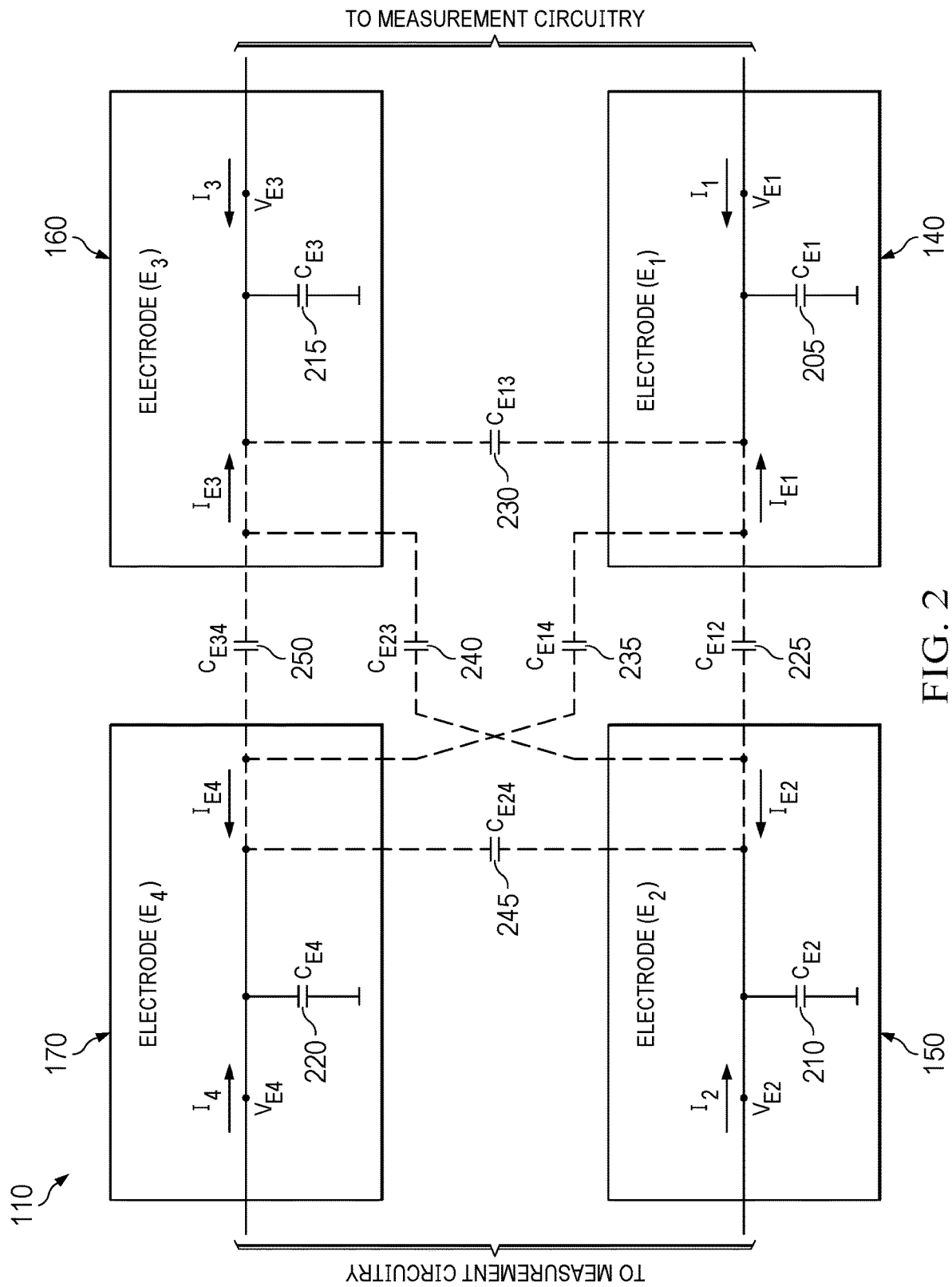
FIG. 2 is a schematic diagram of an example of the electrode network of FIG. 1 including example electrodes and example parasitic capacitances.

FIG. 2 is a schematic diagram of an example of the electrode network 110 of FIG. 1, including the electrodes 140-170 of FIG. 1. In the example of FIG. 2, the first electrode 140 has (or is characterized by) a first example parasitic capacitance ($C_{E1}$) 205, the second electrode 150 has a second example parasitic capacitance ($C_{E2}$) 210, the third electrode 160 has a third example parasitic capacitance ($C_{E3}$) 215, and the fourth electrode 170 has a fourth example parasitic capacitance ($C_{E4}$) 220. In the example of FIG. 2, the parasitic capacitances 205-220 are illustrated as capacitors for clarity. The parasitic capacitances 205-220 are created between each of the electrodes 140-170 and a common terminal that that provides a common potential (e.g., ground).

In the example of FIG. 2, the electrodes 140-170 are coupled by a first example parasitic cross capacitance ($C_{E12}$) 225, a second example parasitic cross capacitance ($C_{E13}$) 230, a third example parasitic cross capacitance ($C_{E14}$) 235, a fourth example parasitic cross capacitance ($C_{E23}$) 240, a fifth example parasitic cross capacitance ($C_{E24}$) 245, and a sixth example parasitic cross capacitance ($C_{E34}$) 250. The parasitic cross capacitance 225-250 are parasitic capacitances, which are illustrated as capacitors for clarity. The parasitic cross capacitance 225-250 are created between each of the electrodes 140-170.

The first parasitic cross capacitance 225 is created between the electrodes 140 and 150. The second parasitic cross capacitance 230 is created between the electrodes 140 and 160. The third parasitic cross capacitance 235 is created between the electrodes 140 and 170. The fourth parasitic cross capacitance 240 is created between the electrodes 150 and 160. The fifth parasitic cross capacitance 245 is created between the electrodes 150 and 170. The sixth parasitic cross capacitance 250 is created between the electrodes 160 and 170.

The parasitic cross capacitances 225-250 may be reduced by repositioning the electrodes 140-170 to be farther apart. However, repositioning the electrodes 140-170 and/or electrical traces coupling the electrodes 140-170 may result in increases in the SoC size. In some examples, such as wearable devices, increasing a SoC size results in excessive discomfort to users. In other examples, increasing the spacing of the electrodes 140-170 decreases accuracy of measurements taken using the electrodes 140-170.

Figure 3:
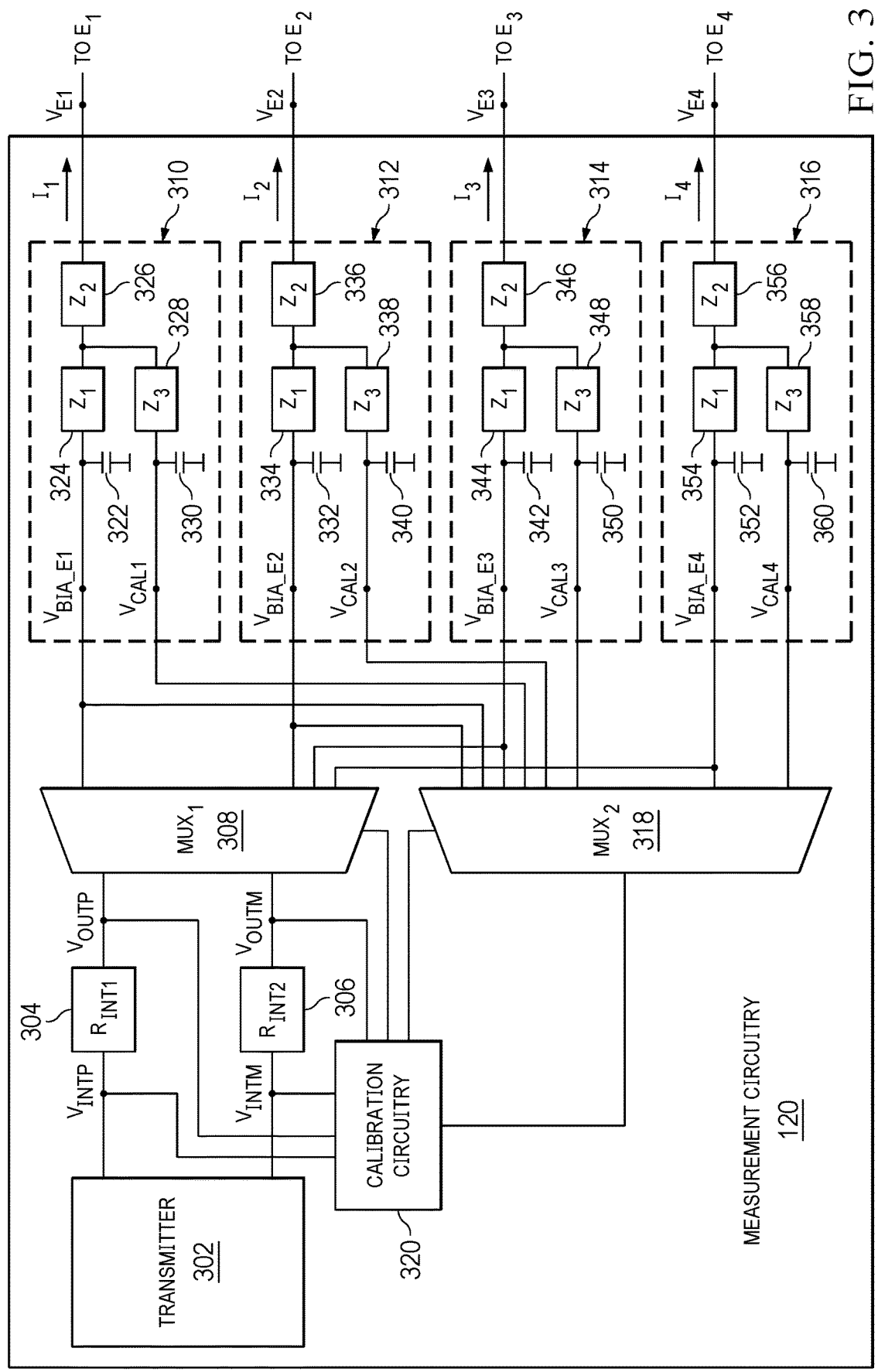
FIG. 3 is a schematic diagram of an example of the measurement circuitry of FIG. 1 including example calibration circuitry that determines the parasitic capacitances of FIG. 2.

FIG. 3 is a schematic diagram of an example of the measurement circuitry 120 of FIG. 1 that may be used to determine the parasitic capacitances 205-250 of FIG. 2. In the example of FIG. 3, the measurement circuitry 120 includes an example transmitter 302, a first example resistor ($R_{INT1}$) 304, a second example resistor ($R_{INT2}$) 306, a first example multiplexer (MUX 1) 308, first example impedance circuitry 310, second example impedance circuitry 312, third example impedance circuitry 314, fourth example impedance circuitry 316, a second example multiplexer ($MUX_2$) 318, and example calibration circuitry 320. The measurement circuitry 120 may be coupled to the electrodes 140-170 of FIGS. 1 and 2.

The transmitter 302 is coupled to the resistors 304 and 306 and the calibration circuitry 320. The transmitter 302 generates an excitation signal. In some examples, the excitation signal is a sinusoidal waveform. In other examples, the excitation signal is a square wave, such as a pulse-width modulation (PWM) signal. The transmitter 302 supplies the excitation signal to the resistors 304 and 306.

The first resistor 304 has a first terminal coupled to a first output of the transmitter 302 and to a first input of the calibration circuitry 320. The resistor 304 has a second terminal coupled to a first input of the first multiplexer 308 and to a second input of the calibration circuitry 320. During operation, a first voltage difference is created or generated between the first and second terminals of the first resistor 304. The first voltage difference is based on a first excitation current of a first excitation signal from the transmitter 302 and a resistance value of the first resistor 304. Accordingly, the first resistor 304 may be referred to as an inline current sensor. The first voltage difference across the first resistor 304 is approximately equal to a first input voltage ($V_{INTP}$) minus a first output voltage ($V_{OUTP}$). The first input voltage is set based on the first excitation current of the first excitation signal from the transmitter 302. The first output voltage is based on the first excitation current and the resistance value of the first resistor 304, and is equal to the first input voltage minus the first voltage difference. In some examples, the calibration circuitry 320 determines the first voltage difference by subtracting the first output voltage from the first input voltage. The first multiplexer 308 receives the first excitation current at its first input, which is coupled to the first resistor 304.

The second resistor 306 has a first terminal coupled to a second output of the transmitter 302 and to a third input of the calibration circuitry 320. The second resistor 306 has a second terminal coupled to a second input of the first multiplexer 308 and to a fourth input of the calibration circuitry 320. During operation, a second voltage difference is created or generated between the first and second terminals of the second resistor 306. The second voltage difference is based on a second excitation current of a second excitation signal from the transmitter 302 and a resistance value of the second resistor 306. Accordingly, the second resistor 306 may be referred to as an inline current sensor. The second voltage difference across the second resistor 306 is approximately equal to a second input voltage ($V_{INTM}$) minus a second output voltage ($V_{OUTM}$). The second input voltage is set based on the second excitation current of the second excitation signal from the transmitter 302. The second output voltage is based on the second excitation current and the resistance value of the second resistor 306, and is equal to the second input voltage minus the second voltage difference. In some examples, the calibration circuitry 320 determines the second voltage difference by subtracting the second output voltage from the second input voltage. The first multiplexer 308 receives the second excitation current at its second input, which is coupled to the second resistor 306.

In the example of FIG. 3, the measurement circuitry 120 includes both resistors 304 and 306. Alternatively, the measurement circuitry 120 includes only one of the resistors 304 or 306, by which the transmitter 302 supplies a single excitation current to the first multiplexer 308.

The first multiplexer 308 has inputs coupled to the resistors 304 and 306, has outputs coupled to the impedance circuitry 310-316, and has a third (control) input coupled to the calibration circuitry 320. The first multiplexer 308 receives the excitation currents, via the resistors 304 and 306, at its first and second inputs, respectively. The first multiplexer 308 supplies one or more of the excitation currents to one or more of the impedance circuitries 310-316 responsive to a control signal from the calibration circuitry 320, at its control input. For example, the first multiplexer 308 supplies the first excitation current, at its first input, to the first impedance circuitry 310. In such an example, the first impedance circuitry 310 may be referred to as excited.

In some examples, the calibration circuitry 320 controls the first multiplexer 308 to supply a positive portion of a differential excitation signal at its first input to a first one of the impedance circuitries 310-316. In such examples, the calibration circuitry 320 controls the first multiplexer 308 to supply a negative portion of the differential excitation signal at its second input to a second one of the impedance circuitries 310-316. For example, the first multiplexer 308 couples the first resistor 304 to the first impedance circuitry 310 and the second resistor 306 to the second impedance circuitry 312. Advantageously, the first multiplexer 308 allows the calibration circuitry 320 control which of the impedance circuitries 310-316 are supplied the excitation currents.

The first impedance circuitry 310 can be coupled to the first electrode 140. The first impedance circuitry 310 is coupled to the multiplexers 308 and 318. In the example of FIG. 3, the first impedance circuitry 310 includes a first example impedance element 324, a second example impedance element 326, a third example impedance element 328. Further, the first impedance circuitry 310 has a first example parasitic capacitance 322 a second example parasitic capacitance 330. The first impedance circuitry 310 receives one of the excitation currents from the first multiplexer 308. The first impedance circuitry 310 supplies the one of the excitation currents to the first electrode 140.

The first parasitic capacitance 322 is created between a first excitation terminal ($V_{BIA\_E1}$) and a common terminal that that provides a common potential (e.g., ground). The first excitation terminal is coupled to the multiplexers 308 and 318 and to the first impedance element 324. In the example of FIG. 3, the first parasitic capacitance 322 is illustrated as a capacitor for clarity.

The first impedance element 324 is coupled to the multiplexers 308 and 318 and to the impedance elements 326 and 328. The first impedance element 324 includes components (not illustrated for simplicity) that create a first desired impedance value ($Z_1$). In some examples, the first impedance element 324 includes a combination of resistors, capacitors, and/or inductors to create the first desired impedance value.

The second impedance element 326 can be coupled to the first electrode 140. The second impedance element 326 is coupled to the impedances 324 and 328. The second impedance element 326 includes components (not illustrated for simplicity) to create a second desired impedance value ($Z_2$). In some examples, the second impedance element 326 includes a combination of resistors, capacitors, and/or inductors to create the second desired impedance value. The second impedance element 326 limits current supplied to the first electrode 140. In some examples, the second impedance element 326 is a safety feature that prevents relatively high currents from being supplied to objects coupled to first electrode 140. For example, in FIG. 1, when the first electrode 140 is coupled to the body 130 of FIG. 1, a relatively high current from the second impedance element 326 could cause harm and/or injury.

The third impedance element 328 is coupled to the second multiplexer 318 and the impedances 324 and 326. The third impedance element 328 includes components (not illustrated for simplicity) to create a third desired impedance value (Z 3). In some examples, the third impedance element 328 includes a combination of resistors, capacitors, and/or inductors to create the third desired impedance value.

The second parasitic capacitance 330 is created between a first calibration terminal ($V_{CAL1}$) and the common terminal. The first calibration terminal is coupled to the second multiplexer 318 and the third impedance element 328. In the example of FIG. 3, the second parasitic capacitance 330 is illustrated as a capacitor for clarity.

The first impedance circuitry 310 provides or supplies a first electrode current ($I_1$) and a first electrode voltage ($V_{E1}$) to or at the first electrode 140. The first electrode current and voltage are based on the excitation currents. In some examples, the excitation currents modify the first electrode current and voltage in response to the multiplexer 308 supplying the excitation currents to one or more of the impedance circuitries 310-316. For example, supplying the first excitation current to the second electrode 150, by the second impedance circuitry 312, causes the parasitic capacitances 205, 210, and 225 of FIG. 2 to modify the first electrode current and voltage.

The second impedance circuitry 312 can be coupled to the second electrode 150. The second impedance circuitry 312 is coupled to the multiplexers 308 and 318. In the example of FIG. 3, the second impedance circuitry 312 includes a fourth example impedance element 334, a fifth example impedance element 336, and a sixth example impedance element 338. Further, the second impedance circuitry 312 has a third example parasitic capacitance 332 and a fourth example parasitic capacitance 340. The second impedance circuitry 312 receives one of the excitation currents from the first multiplexer 308. The second impedance circuitry 312 supplies the one of the excitation currents to the second electrode 150.

The third parasitic capacitance 332 is created between a second excitation terminal ($V_{BIA\_E2}$) and the common terminal. The second excitation terminal is coupled to the multiplexers 308 and 318 and the fourth impedance element 334. In the example of FIG. 3, the third parasitic capacitance 332 is illustrated as a capacitor for clarity.

The fourth impedance element 334 is coupled to the multiplexers 308 and 318 and the impedances 336 and 338. The fourth impedance element 334 includes components (not illustrated for simplicity) to create the first desired impedance value. Accordingly, the impedances 324 and 334 are approximately equal to the first desired impedance value.

The fifth impedance element 336 can be coupled to the second electrode 150. The fifth impedance element 336 is coupled to the impedances 334 and 338. The fifth impedance element 336 includes components (not illustrated for simplicity) to create the second desired impedance value. Accordingly, the impedances 326 and 336 are approximately equal to the second desired impedance value. The fifth impedance element 336 limits current supplied to the second electrode 150. In some examples, the fifth impedance element 336 is a safety feature meant to prevent relatively high currents from being supplied to objects coupled to second electrode 150.

The sixth impedance element 338 is coupled to the second multiplexer 318 and the impedances 334 and 336. The sixth impedance element 338 includes components (not illustrated for simplicity) to create the third desired impedance value. Accordingly, the impedances 328 and 338 are approximately equal to the third desired impedance value.

The fourth parasitic capacitance 340 is created between a second calibration terminal ($V_{CAL2}$) and the common terminal. The second calibration terminal is coupled to the second multiplexer 318 and the sixth impedance element 338. In the example of FIG. 3, the fourth parasitic capacitance 340 is illustrated as a capacitor for clarity.

The second impedance circuitry 312 provides or supplies a second electrode current ($I_2$) and a second electrode voltage ($V_{E2}$) to or at the second electrode 150. The second electrode current and voltage are based on the excitation currents. In some examples, the excitation currents modify the second electrode current and voltage in response to the multiplexer 308 supplying the excitation currents to one or more of the impedance circuitries 310-316.

The third impedance circuitry 314 can be coupled to the third electrode 160. The third impedance circuitry 314 is coupled to the multiplexers 308 and 318. In the example of FIG. 3, the third impedance circuitry 314 includes a seventh example impedance element 344, an eighth example impedance element 346, a ninth example impedance element 348. Further, the third impedance circuitry 314 has a fifth example parasitic capacitance 342 and a sixth example parasitic capacitance 350. The third impedance circuitry 314 receives one of the excitation currents from the first multiplexer 308. The third impedance circuitry 314 supplies the one of the excitation currents to the third electrode 160.

The fifth parasitic capacitance 342 is created between a third excitation terminal ($V_{BIA\_E3}$) and the common terminal. The third excitation terminal is coupled to the multiplexers 308 and 318 and the seventh impedance element 344. In the example of FIG. 3, the fifth parasitic capacitance 342 is illustrated as a capacitor for clarity.

The seventh impedance element 344 is coupled to the multiplexers 308 and 318 and the impedances 346 and 348. The seventh impedance element 344 includes components (not illustrated for simplicity) to create the first desired impedance value. Accordingly, the impedances 324, 334, and 344 are approximately equal to the first desired impedance value.

The eighth impedance element 346 is coupled to the third electrode 160 and the impedances 344 and 348. The eighth impedance element 346 includes components (not illustrated for simplicity) to create the second desired impedance value. Accordingly, the impedances 326, 336, and 346 are approximately equal to the second desired impedance value. The eighth impedance element 346 limits current supplied to the third electrode 160. In some examples, the eighth impedance element 346 is a safety feature meant to prevent relatively high currents from being supplied to objects coupled to third electrode 160.

The ninth impedance element 348 is coupled to the second multiplexer 318 and the impedances 344 and 346. The ninth impedance element 348 includes components (not illustrated for simplicity) to create the third desired impedance value. Accordingly, the impedances 328, 338, and 348 are approximately equal to the third desired impedance value.

The sixth parasitic capacitance 350 is created between a third calibration terminal ($V_{CAL3}$) and the common terminal. The third calibration terminal is coupled to the second multiplexer 318 and the ninth impedance element 348. In the example of FIG. 3, the sixth parasitic capacitance 350 is illustrated as a capacitor for clarity.

The third impedance circuitry 314 provides or supplies a third electrode current (I 3) and a third electrode voltage ($V_{E3}$) to or at the third electrode 160. The third electrode current and voltage are based on the excitation currents. In some examples, the excitation currents modify the third electrode current and voltage in response to the multiplexer 308 supplying the excitation currents to one or more of the impedance circuitries 310-316.

The fourth impedance circuitry 316 can be coupled to the fourth electrode 170. The fourth impedance circuitry 316 is coupled to the multiplexers 308 and 318. In the example of FIG. 3, the fourth impedance circuitry 316 includes a tenth example impedance element 354, an eleventh example impedance element 356, and a twelfth example impedance element 358. Further, the fourth impedance circuitry 316 has a seventh example parasitic capacitance 352 and an eighth example parasitic capacitance 360. The fourth impedance circuitry 316 receives one of the excitation currents from the first multiplexer 308. The fourth impedance circuitry 316 supplies the one of the excitation currents to the fourth electrode 170.

The seventh parasitic capacitance 352 is created between a fourth excitation terminal ($V_{BIA\_E4}$) and the common terminal. The fourth excitation terminal is coupled to the multiplexers 308 and 318 and the tenth impedance element 354. In the example of FIG. 3, the seventh parasitic capacitance 352 is illustrated as a capacitor for clarity.

The tenth impedance element 354 is coupled to the multiplexers 308 and 318 and the impedances 356 and 358. The tenth impedance element 354 includes components (not illustrated for simplicity) to create the first desired impedance value. Accordingly, the impedances 324, 334, 344, and 354 are approximately equal to the first desired impedance value.

The eleventh impedance element 356 is coupled to the fourth electrode 170 and the impedances 354 and 358. The eleventh impedance element 356 includes components (not illustrated for simplicity) to create the second desired impedance value. Accordingly, the impedances 326, 336, 346, and 356 are approximately equal to the second desired impedance value. The eleventh impedance element 356 limits current supplied to the fourth electrode 170. In some examples, the eleventh impedance element 356 is a safety feature meant to prevent relatively high currents from being supplied to objects coupled to fourth electrode 170.

The twelfth impedance element 358 is coupled to the second multiplexer 318 and the impedances 354 and 356. The twelfth impedance element 358 includes components (not illustrated for simplicity) to create the third desired impedance value. Accordingly, the impedances 328, 338, 348, and 358 are approximately equal to the third desired impedance value.

The eighth parasitic capacitance 360 is created between a fourth calibration terminal ($V_{CAL4}$) and the common terminal. The fourth calibration terminal is coupled to the second multiplexer 318 and the twelfth impedance element 358. In the example of FIG. 3, the eighth parasitic capacitance 360 is illustrated as a capacitor for clarity.

Advantageously, the parasitic capacitances 322 and 330 are generated by similar couplings and proximity to the common terminal. Accordingly, the parasitic capacitances 322 and 330 are approximately equal to each other. Similarly, the parasitic capacitances 332 and 340 are approximately equal to each other. The parasitic capacitances 342 and 350 are approximately equal to each other, and the parasitic capacitances 352 and 360 are approximately equal to each other.

The fourth impedance circuitry 316 provides or supplies a fourth electrode current ($I_4$) and a fourth electrode voltage ($V_{E4}$) to or at the fourth electrode 170. The fourth electrode current and voltage are based on the excitation currents. In some examples, the excitation currents modify the second electrode current and voltage in response to the multiplexer 308 supplying the excitation currents to one or more of the impedance circuitries 310-316.

The second multiplexer 318 is coupled to the impedance circuitry 310-316 and the calibration circuitry 320. The second multiplexer 318 couples one or more of the excitation terminals and/or calibration terminals of the impedance circuitries 310-316 to the calibration circuitry 320. In some examples, the calibration circuitry 320 may be coupled to all of the impedance circuitry 310-316, such as to remove the multiplexer 318. In other examples second multiplexer 308 supplies voltages of the excitation terminals and calibration terminals to the calibration circuitry 320.

The calibration circuitry 320 is coupled to the resistors 304 and 306 and the multiplexers 308 and 318. The calibration circuitry 320 controls the multiplexers 308 and 318. The calibration circuitry 320 controls the first multiplexer 308 to determine which of the impedance circuitries 310-316 receive the excitation currents. The calibration circuitry 320 controls the second multiplexer 318 to select voltages of the excitation terminals and calibration terminals of the impedance circuitries 310-316.

The calibration circuitry 320 determines magnitudes of the parasitic capacitances 205-250 of FIG. 2 and the parasitic capacitances 322, 330, 332, 340, 342, 350, 352, and 360 based on the voltage differences across the resistors 304 and 306 and voltages supplied by the second multiplexer 318. An example of the calibration circuitry 320 is described in further detail in FIG. 4, below. An example determination of the parasitic capacitances 205-250, 322, 330, 332, 340, 342, 350, 352, and 360 are described in detail in connection with FIG. 4, below.

Figure 4:
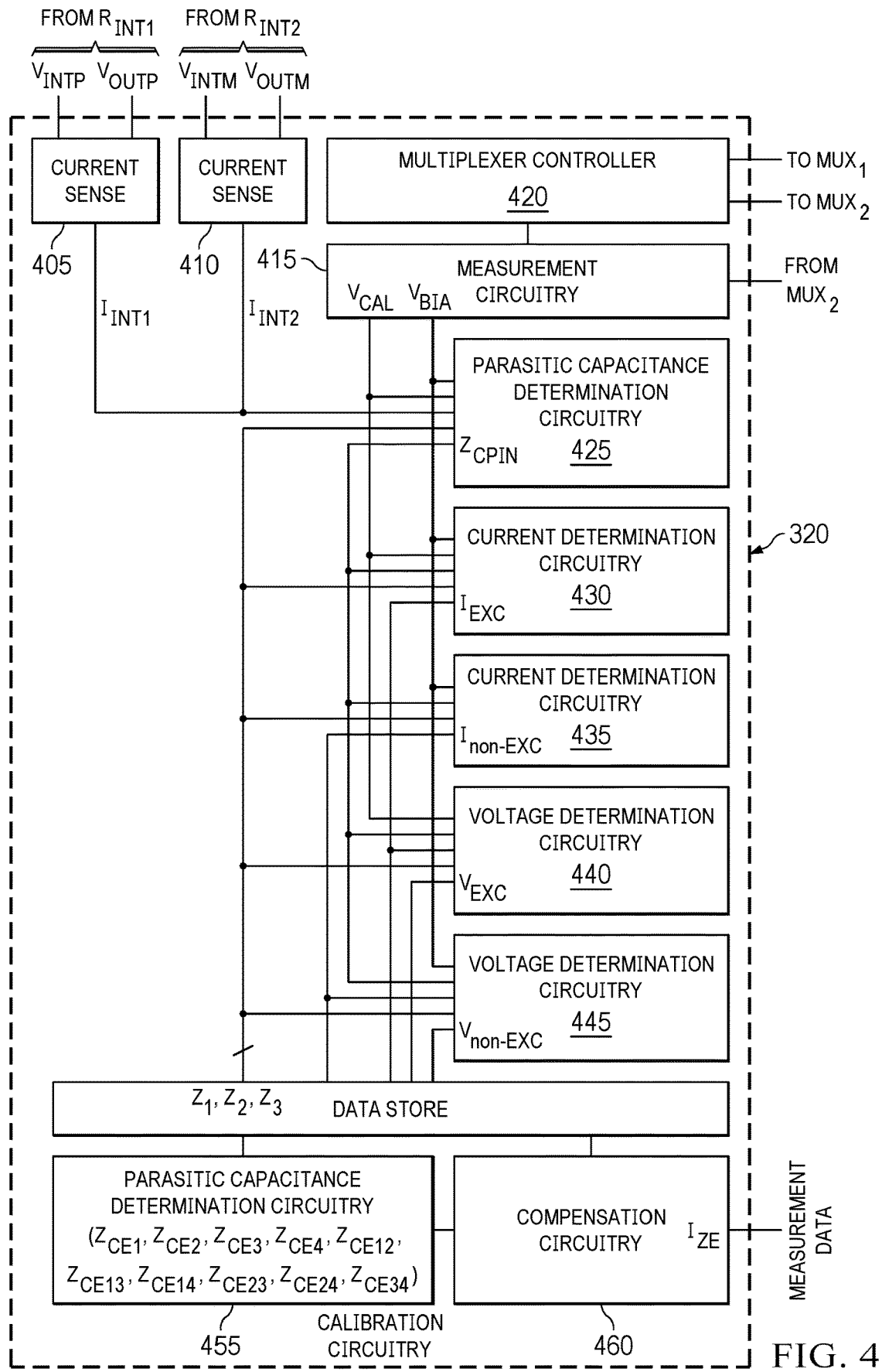
FIG. 4 is a block diagram of an example of the calibration circuitry of FIG. 3.

FIG. 4 is a block diagram of the calibration circuitry 320 of FIG. 3 that can determine the parasitic capacitances 205-250 of FIG. 2. The calibration circuitry 320 may be instantiated (e.g., creating an instance of, bring into being for any length of time, materialize, implement, etc.) by processor circuitry such as a central processing unit executing instructions. Additionally or alternatively, the calibration circuitry 320 may be instantiated (e.g., creating an instance of, bring into being for any length of time, materialize, implement, etc.) by an ASIC or an FPGA structured to perform operations corresponding to the instructions. Some or all of the calibration circuitry 320 may, thus, be instantiated at the same or different times. Some or all of the circuitry may be instantiated, for example, in one or more threads executing concurrently on hardware and/or in series on hardware. Moreover, in some examples, some or all of the calibration circuitry 320 may be implemented by microprocessor circuitry executing instructions to implement one or more virtual machines and/or containers.

In the example of FIG. 4, the calibration circuitry 320 includes first example current sense circuitry 405, second example current sense circuitry 410, example measurement circuitry 415, an example multiplexer controller 420, first example parasitic capacitance circuitry 425, first example current determination circuitry 430, second example current determination circuitry 435, first voltage determination circuitry 440, second example voltage determination circuitry 445, an example data store 450, second example parasitic capacitance determination circuitry 455, and example compensation circuitry 460. The calibration circuitry 320 determines magnitudes of the parasitic capacitances 205-250 of FIGS. 2 and 322, 330, 332, 340, 342, 350, 352, and 360 of FIG. 3 based on the excitation currents from the transmitter 302 of FIG. 3 and voltage measurements of the impedance circuitries 310-316 of FIG. 3.

The first current sense circuitry 405 has inputs coupled, respectively, to the first and second terminals of the first resistor 304 of FIG. 3, and has an output coupled to the first parasitic capacitance determination circuitry 425. The first current sense circuitry 405 receives the first voltage input (V INT p) and the first voltage output (Vou T p), from the first resistor 304. The first current sense circuitry 405 determines a first excitation current value (Lyn) based on the voltages from the first resistor 304. The first excitation current value represents a current of the excitation signal the transmitter 302 supplies to the first resistor 304. In some examples, the first current sense circuitry 405 determines the first excitation current value by dividing a difference between the first voltage input and the first voltage output by a resistance of the first resistor ($R_{INT1}$) 302. In such examples, the first current sense circuitry 405 may use Equation (1), below. The first current sense circuitry 405 supplies the first excitation current value to the first parasitic capacitance circuitry 425.

$$I_{RINT1} = \frac{V_{INTP} - V_{OUTP}}{R_{INT1}}, \qquad \text{Equation (1)}$$

In some examples, the first current sense circuitry 405 is instantiated by processor circuitry executing first current sense instructions and/or performing operations such as those represented by the flowcharts of FIGS. 5A-6C.

The second current sense circuitry 410 is coupled to the second resistor 304 of FIG. 3 and the first parasitic capacitance determination circuitry 425. The second current sense circuitry 410 receives the second voltage input ($V_{INTM}$) and the second voltage output ($V_{OUTM}$), from the second resistor 306. The second current sense circuitry 410 determines a second excitation current value ($I_{INT2}$) based on the voltages from the second resistor 306. The second excitation current value represents a current of the excitation signal supplied to the second resistor 306. In some examples, the second current sense circuitry 410 determines the second excitation current value by dividing a difference between the second voltage input and the second voltage output by a resistance of the second resistor ($R_{INT2}$) 306. In such examples, the second current sense circuitry 410 may use Equation (2), below. The second current sense circuitry 410 supplies the second excitation current value to the first parasitic capacitance circuitry 425.

$$I_{RINT2} = \frac{V_{INTM} - V_{OUTM}}{R_{INT2}}, \qquad \text{Equation (2)}$$

In some examples, the second current sense circuitry 410 is instantiated by processor circuitry executing second current sense instructions and/or configured to perform operations such as those represented by the flowcharts of FIGS. 5A-6C.

In the example of FIG. 4, the current sense circuitries 405 and 410 use Equations (1) and (2), above, to determine excitation current values representative of the excitation signal from the transmitter 302. Alternatively, another method of determining currents and/or voltages representative of the excitation signal may be used in accordance with the description herein. For example, the calibration circuitry 320 uses current values and/or voltage values stored in memory.

The measurement circuitry 415 can be coupled to second multiplexer 318 of FIG. 3. The measurement circuitry 415 is coupled to the multiplexer controller 420 and the circuitries 425-445. In FIG. 3, the second multiplexer 318 selectively provides signals at or from the excitation terminals and the calibration terminals of the impedance circuitries 310-316 to the calibration circuitry 320. In some examples, the measurement circuitry 415 samples and holds voltages of the excitation terminals and the calibration terminals to respectively generate a bias voltage value ($V_{BIA}$) and a calibration voltage value ($V_{CAL}$). The measurement circuitry 415 supplies the bias voltage value and the calibration voltage value to the circuitries 425-445. In some examples, the measurement circuitry 415 may include analog-to-digital converter (ADC) circuitry (not illustrated) to convert analog voltages of the excitation and calibration terminals to digital values. In such examples, the operations of the circuitries 425-445 may be performed by digital circuitry, such as a digital signal processor, microcontroller unit, processor circuitry, etc.

The measurement circuitry 415 provides control indications to the multiplexer controller 420. Responsive to the control indications the multiplexer controller 420 provides the control signals to the first multiplexer 308 and the second multiplexer 318, resulting in the signal provided from the multiplexer 318 to the measurement circuitry 415. For example, responsive to a first control indication, the multiplexer controller 420 provides first control signals. The first control signals control the first multiplexer 308 and the second multiplexer 318 to operate such the measurement circuitry 415 samples signals at the first excitation terminal ($V_{BIA\_E1}$) and the first calibration terminal ($V_{CAL1}$) of the first impedance circuitry 310, to generate the bias voltage value and the calibration voltage value. In such an example, responsive to a second control indication, the multiplexer controller 420 provides second control signals. The second control signals control the first multiplexer 308 and the second multiplexer 318 to operate such the measurement circuitry 415 samples signals at the second excitation terminal ($V_{BIA\_E2}$) and the second calibration terminal ($V_{CAL2}$) of the second impedance circuitry 312. In some examples, the measurement circuitry 415 may use a sequencing process to generate the control indications. In such examples, the measurement circuitry 415 may generate control indications to traverse all of the excitation terminals and the calibration terminals at predefined intervals. The measurement circuitry 415 supplies the control indications to the multiplexer controller 420.

In the example of FIG. 4, the measurement circuitry 415 generates the bias voltage value to represent a voltage of one of the excitation terminals of the impedance circuitries 310-316 and the calibration voltage value to represent a voltage of one of the calibration terminals of the impedance circuitries 310-316. Alternatively, the calibration circuitry 320 may include additional routings and/or circuitry to supply a plurality of voltage values representing a plurality of the excitation terminals and/or calibration terminals of the impedance circuitries 310-316. In some examples, the measurement circuitry 415 is instantiated by processor circuitry executing measurement instructions and/or performing operations such as those represented by the flowcharts of FIGS. 5A-6C.

The multiplexer controller 420 is coupled to the multiplexers 308 and 318 and the measurement circuitry 415. The multiplexer controller 420 receives indications from the measurement circuitry 415. The multiplexer controller 420 controls the multiplexers 308 and 318 based on the indications. In some examples, the multiplexer controller 420 converts the indications into multi-bit control signals. In such examples, the multiplexer controller 420 supplies the multi-bit control signals to the multiplexers 308 and 318 to modify operations of the measurement circuitry 120 of FIGS. 1 and 3. In some examples, the multiplexer controller 420 is instantiated by processor circuitry executing multiplexer controller instructions and/or configured to perform operations such as those represented by the flowcharts of FIGS. 5A-6C.

The first parasitic capacitance determination circuitry 425 is coupled to the circuitries 405-415 and 430-445 and the data store 450. The first parasitic capacitance determination circuitry 425 receives the excitation current values from the current sense circuitries 405 and 410. The first parasitic capacitance determination circuitry 425 receives the bias voltage value and the calibration voltage value from the measurement circuitry 415. The first parasitic capacitance determination circuitry 425 receives the first desired impedance value ($Z_1$) from the data store 450. The first desired impedance value represents a magnitude of the impedances 324, 334, 344, and 354 of FIG. 3. The first parasitic capacitance determination circuitry 425 receives the third desired impedance value ($Z_3$) from the data store 450. The third desired impedance value represents a magnitude of the impedances 328, 338, 348, and 358 of FIG. 3. The first parasitic capacitance determination circuitry 425 supplies the parasitic impedance value to the determination circuitries 430-445.

The first parasitic capacitance determination circuitry 425 determines a parasitic impedance value ($Z_{CPIN}$) of the parasitic capacitances 322, 330, 332, 340, 342, 352, and 360. Advantageously, the parasitic capacitances 322 and 330 are approximately equal. The parasitic capacitances 332 and 340 are approximately equal. The parasitic capacitances 342 and 350 are approximately equal, and the parasitic capacitances 352 and 360 are approximately equal. In some examples, the first parasitic capacitance determination circuitry 425 uses Kirchhoff's current law to determine the parasitic impedance of the parasitic capacitances (Zcp N) 322, 330, 332, 340, 342, 352, and 360. In such examples, the first parasitic capacitance determination circuitry 425 sets current supplied to one of the impedance circuitries 310-316 equal to a summation of possible paths of the current.

In an example operation, the first multiplexer 308 supplies the first excitation current (TINTO to the first impedance circuitry 310. In such a configuration, the first excitation current has a first path through the first parasitic capacitance 322 and a second path through the first impedance element 324. A first current, through the first path, is approximately equal to a voltage of the first excitation terminal ($V_{BIA\_E1}$) divided by the parasitic impedance ($Z_{CPIN}$) of the first parasitic capacitance 322. A second current, through the second path, is approximately equal to a voltage difference across the first impedance element 324 divided by the first desired impedance value ($Z_1$). The voltage difference across the first impedance element 324 is approximately equal to the voltage of the first excitation terminal minus a node voltage of a terminal coupling the impedances 324-328. The node voltage is approximately equal to a voltage of the first calibration terminal ($V_{CAL1}$) plus a voltage difference across the third impedance element 328 resulting from current through the second parasitic capacitance 330. Advantageously, the impedances of the parasitic capacitances 322 and 330 are approximately equal, such as both may be approximated to the parasitic impedance. Accordingly, the voltage difference across the third impedance element 328 is approximately equal to the third desired impedance value (Z 3) times the voltage of the first calibration terminal divided by the parasitic impedance. Equation (3), below, illustrates applying Kirchhoff's current law to the first path and the second path, described above. In such an operation, the first parasitic capacitance determination circuitry 425 may solve Equation (3), below, for the parasitic impedance $Z_{CPIN}$. The first parasitic capacitance determination circuitry 425 supplies a parasitic impedance value to the determination circuitries 430-445. The parasitic impedance value represents the parasitic impedance $Z_{CPIN}$.

$$I_{RINT1} = \frac{V_{BIA\_E1}}{Z_{CPIN}} + \frac{V_{BIA\_E1} - V_{CAL1} *\left(1 + \frac{Z_3}{Z_{CPIN}}\right)}{Z_1}, \quad \text{Equation (3)}$$

Alternatively, the first parasitic capacitance determination circuitry 425 may use another example operation of the measurement circuitry 120 to determine the parasitic impedance of the parasitic capacitances 322, 330, 332, 340, 342, 352, and 360 in accordance with the teachings described herein. In some examples, the first parasitic capacitance determination circuitry 425 is instantiated by processor circuitry executing first parasitic capacitance determination instructions and/or configured to perform operations such as those represented by the flowcharts of FIGS. 5A-6C.

The first current determination circuitry 430 is coupled to the circuitries 415, 425, and 435-445 and the data store 450. The first current determination circuitry 430 receives the bias voltage value and the calibration voltage value from the measurement circuitry 415. The first current determination circuitry 430 receives the parasitic impedance value from the first parasitic capacitance circuitry 425. The first current determination circuitry 430 receives the first desired impedance value ($Z_1$) from the data store 450. The first current determination circuitry 430 receives the third desired impedance value (Z 3) from the data store 450. The first current determination circuitry 430 determines an excited electrode current ($I_{EXC}$).

The excited electrode current is a current supplied to one of the electrodes 140-170 of FIG. 1, by one of the impedance circuitries 310-316, in response to the first multiplexer 308 suppling one of the excitation currents to the one of the impedance circuitries 310-316. In some examples, the first current determination circuitry 430 uses Kirchhoff's current law to determine the excited electrode current. In such examples, the first current determination circuitry 430 sets current from the one of the impedance circuitries 310-316 equal to a summation of possible paths of the current.

In an example operation, the first multiplexer 308 supplies the first excitation current to the first impedance circuitry 310. Accordingly, the first electrode current ($I_1$) is approximately equal to current supplied by a first path from the first impedance element 324 minus current supplied to the second parasitic capacitance 330 by a second path. The first path supplies a current approximately equal to a voltage difference across the first impedance element 324 divided by the first desired impedance value ($Z_1$). The voltage difference across the first impedance element 324 is approximately equal to the voltage of the first excitation terminal minus a node voltage of a terminal coupling the impedances 324-328. The node voltage is approximately equal to a voltage of the first calibration terminal ($V_{CAL1}$) plus a voltage difference across the third impedance element 328 caused by current through the second parasitic capacitance 330.

Advantageously, the impedances of the parasitic capacitances 322 and 330 are approximately equal, such as both may be approximated to the parasitic impedance. Accordingly, the voltage difference across the third impedance element 328 is approximately equal to the third desired impedance value ($Z_3$) times the voltage of the first calibration terminal divided by the parasitic impedance. The second path is equal to the current through the second parasitic capacitance 330, which as described above, is equal to the voltage of the first calibration terminal divided by the parasitic impedance. Equation (4), below, illustrates applying Kirchhoff's current law to the first path and the second path, described above. In such an operation, the first current determination circuitry 430 may solve Equation (4), below, for the first electrode current, which is more generally referred to as the excited electrode current. The first current determination circuitry 430 supplies an excited electrode current value to the first voltage determination circuitry 440 and the data store 450. The excited electrode current value represents the excited electrode current.

$$I_1 = \frac{V_{BIA\_E1} - V_{CAL1} * \left(1 + \frac{Z_3}{Z_{CPIN}}\right)}{Z_1} - \frac{V_{CAL1}}{Z_{CPIN}}, \quad \text{Equation (4)}$$

Alternatively, the first current determination circuitry 430 may use another example operation of the measurement circuitry 120 to determine the excited electrode current in accordance with the teachings described herein. In some examples, the first current determination circuitry 430 is instantiated by processor circuitry executing first current determination instructions and/or configured to perform operations such as those represented by the flowcharts of FIGS. 5A-6C.

In other example operations, the first current determination circuitry 430 may use Equation (4), above, in accordance to the teachings described herein, to determine two or more excited electrode currents. In such examples, the first multiplexer 308 supplies the first excitation current to a first one of the impedance circuitries 310-316 and the second excitation current to a second one of the impedance circuitries 310-316. For example, the first current determination circuitry 430 determines the first electrode current and the second electrode current using Equation (4), above, when the excitation currents are supplied to the impedance circuitries 310 and 312.

The second current determination circuitry 435 is coupled to the circuitries 415, 425, 430, 440, and 445 and the data store 450. The second current determination circuitry 435 receives the bias voltage value from the measurement circuitry 415. The second current determination circuitry 435 receives the parasitic impedance value from the first parasitic capacitance circuitry 425. The second current determination circuitry 435 receives the first desired impedance value ($Z_1$) from the data store 450. The second current determination circuitry 435 receives the third desired impedance value ($Z_3$) from the data store 450. The second current determination circuitry 435 determines a non-excited electrode current ($I_{non-EXC}$).

The non-excited electrode current is a current supplied by one of the electrodes 140-170 in response to the first multiplexer 308 supplying the excitation signal to a different one of the impedance circuitries 310-316. In some examples, the second current determination circuitry 435 uses Kirchhoff's current law to determine the non-excited electrode current. In such examples, the second current determination circuitry 435 sets current from the one of the impedance circuitries 310-316 equal to a summation of possible paths of the current.

In an example operation, the first multiplexer 308 supplies the first excitation current to the first impedance circuitry 310 and none of the excitation currents to the third impedance circuitry 314. In such a configuration, the third electrode current ($I_3$) is approximately equal to current supplied by a first path through the seventh impedance element 344 of FIG. 3 and current supplied by a second path through the ninth impedance element 348 of FIG. 3. A first current, through the first path, is approximately equal to a voltage of the third excitation terminal ($V_{BIA\_E3}$) divided by the parasitic impedance ($Z_{CPIN}$) of the fifth parasitic capacitance 342.

A second current, through the second path, is approximately equal to the voltage of the third excitation terminal plus the first current times the first desired impedance value ($Z_1$) divided by a total impedance of the second path. The total impedance of the second path is a series combination of the third desired impedance value ($Z_3$) of the ninth impedance element 348 and the parasitic impedance of the sixth parasitic capacitance 350 of FIG. 3. Equation (5), below, illustrates applying Kirchhoff's current law to the first path and the second path, described above. In such an operation, the second current determination circuitry 435 solves Equation (5), below, for the third electrode current, which is more generally referred to as the non-excited electrode current. The second current determination circuitry 435 supplies a non-excited electrode current value to the second voltage determination circuitry and the data store 450. The non-excited electrode current represents the non-excited electrode current.

$$I_3 = -\frac{V_{BIA\_E3}}{Z_{CPIN}} - \frac{V_{BIA\_E3} * \left(1 + \frac{Z_1}{Z_{CPIN}}\right)}{Z_{CPIN} + Z_3}, \quad \text{Equation (5)}$$

Alternatively, the second current determination circuitry 435 may use another example operation of the measurement circuitry 120 to determine the non-excited electrode current in accordance with the teachings described herein. In some examples, the second current determination circuitry 435 is instantiated by processor circuitry executing second current determination instructions and/or configured to perform operations such as those represented by the flowcharts of FIGS. 5A-6C.

In other example operations, the second current determination circuitry 435 may use Equation (5), above, in accordance with the teachings described herein, to determine two or more non-excited electrode currents. In such examples, the first multiplexer 308 supplies the first excitation current to a first one of the impedance circuitries 310-316 and the second excitation current to a second one of the impedance circuitries 310-316. For example, the second current determination circuitry 435 determines the third electrode current and the fourth electrode current using Equation (5), above, when the excitation currents are supplied to the impedance circuitries 310 and 312.

The first voltage determination circuitry 440 is coupled to the measurement circuitry 415, the circuitries 425 and 430, and the data store 450. The first voltage determination circuitry 440 receives the calibration voltage value from the measurement circuitry 415. The first voltage determination circuitry 440 receives the parasitic impedance value from the first parasitic capacitance circuitry 425. The first voltage determination circuitry 440 receives the excited electrode current value from the first current determination circuitry 430. The first voltage determination circuitry 440 receives the second desired impedance value ($Z_2$) from the data store 450. The first voltage determination circuitry 440 receives the third desired impedance value ($Z_3$) from the data store 450. The first voltage determination circuitry 440 determines an excited electrode voltage ($V_{ECC}$).

The excited electrode voltage is a voltage of a terminal coupling the electrodes 140-170 to one of the impedance circuitries 310-316, in response to the first multiplexer 308 supplying the excitation signal to the one of the impedance circuitries 310-316. In some examples, the first voltage determination circuitry 440 uses Kirchhoff's voltage law to determine the excited electrode voltage. In such examples, the first voltage determination circuitry 440 determines the excited electrode voltage by adding voltage contributions of impedances of the impedance circuitries 310-316.

In an example operation, the first multiplexer 308 supplies the first excitation current to the first impedance circuitry 310. Accordingly, the first electrode voltage ($V_{E1}$) is approximately equal to the voltage of the first calibration terminal ($V_{CAL1}$) plus a first voltage difference across the third impedance element 328 minus a second voltage difference across the second impedance element 326. The first voltage difference is approximately equal to the third desired impedance value times a current through the second parasitic capacitance 330, which is the voltage of the first calibration terminal divided by the parasitic impedance. The second voltage difference is approximately equal to the first electrode current ($I_1$) times the second desired impedance value ($Z_2$) of the second impedance element 326. The first electrode current is approximately equal to the excited electrode current from the first current determination circuitry 430. Equation (6), below, illustrates applying Kirchhoff's voltage law to determine the first electrode voltage, as described above. In such an operation, the first voltage determination circuitry 440 may solve Equation (6), below, for the first electrode voltage, which may be more generally referred to as the excited electrode voltage. The first voltage determination circuitry 440 supplies an excited electrode voltage value to the data store 450. The excited electrode voltage value represents the excited electrode voltage.

$$V_{E1} = V_{CAL1} * \left(1 + \frac{Z_3}{Z_{CPIN}}\right) - I_1 * Z_2, \quad \text{Equation (6)}$$

Alternatively, the first voltage determination circuitry 440 may use another example operation of the measurement circuitry 120 to determine the excited electrode voltage in accordance with the teachings described herein. In some examples, the first voltage determination circuitry 440 is instantiated by processor circuitry executing first voltage determination instructions and/or configured to perform operations such as those represented by the flowcharts of FIGS. 5A-6C.

In other example operations, the first voltage determination circuitry 440 may use Equation (6), above, in accordance with the teachings described herein, to determine two or more excited electrode voltages. In such examples, the first multiplexer 308 supplies the first excitation current to a first one of the impedance circuitries 310-316 and the second excitation current to a second one of the impedance circuitries 310-316. For example, the first voltage determination circuitry 440 determines the first electrode voltage and the second electrode voltage using Equation (6), above, when the excitation currents are supplied to the impedance circuitries 310 and 312.

The second voltage determination circuitry 445 is coupled to the measurement circuitry 415, the circuitries 425 and 435, and the data store 450. The second voltage determination circuitry 445 receives the bias voltage from the measurement circuitry 415. The second voltage determination circuitry 445 receives the parasitic impedance from the first parasitic capacitance circuitry 425. The second voltage determination circuitry 445 receives the indication of the non-excited electrode current from the second current determination circuitry 435. The second voltage determination circuitry 445 receives the value of the first desired impedance value ($Z_1$) from the data store 450. The second voltage determination circuitry 445 receives the value of the second desired impedance value ($Z_2$) from the data store 450. The second voltage determination circuitry 445 determines a non-excited electrode voltage ($V_{non\text{-}EXC}$). The second voltage determination circuitry 445 supplies an indication of the non-excited electrode voltage to the data store 450.

The non-excited electrode voltage is a voltage of a terminal coupling the electrodes 140-170 to one of the impedance circuitries 310-316, in response to the first multiplexer 308 suppling the excitation signal to a different one of the impedance circuitries 310-316. In some examples, the second voltage determination circuitry 445 uses Kirchhoff's voltage law to determine the non-excited electrode voltage. In such examples, the second voltage determination circuitry 445 determines the non-excited electrode voltage by adding voltage contributions of impedances of the impedance circuitries 310-316.

In an example operation, the first multiplexer 308 supplies the first excitation current to the first impedance circuitry 310 and none of the excitation currents to the third impedance circuitry 314. In such a configuration, the third electrode voltage ($V_{E3}$) is approximately equal to the voltage of the third excitation terminal ($V_{BIAE3}$) plus a first voltage difference across the seventh impedance element 344 minus a second voltage difference across the eighth impedance element 346. The first voltage difference is approximately equal to the first desired impedance value ($Z_1$) times a current through the fifth parasitic capacitance 342, which is the voltage of the third excitation terminal divided by the parasitic impedance.

The second voltage difference is approximately equal to the third electrode current ($I_3$) times the second desired impedance value ($Z_2$) of the eighth impedance element 346. The third electrode current is approximately equal to the non-excited electrode current from the second current determination circuitry 435. Equation (7), below, illustrates applying Kirchhoff s voltage law to determine the third electrode voltage, as described above. In such an operation, the second voltage determination circuitry 445 may solve Equation (7), below, for the third electrode voltage, which may be more generally referred to as the non-excited electrode voltage.

$$V_{E3} = V_{BIA\_E3} * \left(1 + \frac{Z1}{Z_{CPIN}}\right) - I_3 * Z_2, \qquad \text{Equation (7)}$$

Alternatively, the second voltage determination circuitry 445 may use another example operation of the measurement circuitry 120 to determine the non-excited electrode voltage in accordance with the teachings described herein. In some examples, the second voltage determination circuitry 445 is instantiated by processor circuitry executing second voltage determination instructions and/or configured to perform operations such as those represented by the flowcharts of FIGS. 5A-6C.

In other example operations, the second voltage determination circuitry 445 may use Equation (7), above, in accordance with the teachings described herein, to determine two or more non-excited electrode voltages. In such examples, the first multiplexer 308 supplies the first excitation current to a first one of the impedance circuitries 310-316 and the second excitation current to a second one of the impedance circuitries 310-316. For example, the second voltage determination circuitry 445 determines the third electrode voltage and the fourth electrode voltage using Equation (7), above, when the excitation currents are supplied to the impedance circuitries 310 and 312.

The data store 450 is coupled to the circuitries 425-445, 455, and 460. The data store 450 supplies the desired impedance values to the circuitries 425-445. The data store 450 receives excited electrode current values from the first current determination circuitry 430. The data store 450 receives non-excited electrode current values from the second current determination circuitry 435. The data store 450 receives excited electrode voltage values from the first voltage determination circuitry 440. The data store 450 receives non-excited electrode voltage values from the second voltage determination circuitry 445. The data store 450 stores one or more sets of the electrode current values and voltage values of the determination circuitries 430-445. The data store 450 supplies the electrode current values and voltage values to the second parasitic capacitance determination circuitry 455 and the compensation circuitry 460. Advantageously, the data store 450 stores a plurality of electrode voltage values representing a plurality of configurations of the measurement circuitry 120. In some examples, the data store 450 may receive and store parasitic impedance values of the parasitic capacitances 205-250 from the second parasitic capacitance determination circuitry 455.

The second parasitic capacitance determination circuitry 455 is coupled to the data store 450 and the compensation circuitry 460. The second parasitic capacitance determination circuitry 455 receives electrode current values and voltage values from the data store 450. The second parasitic capacitance determination circuitry 455 determines parasitic impedances of the parasitic capacitances 205-250. The second parasitic capacitance determination circuitry 455 supplies the parasitic impedance values to the compensation circuitry 460 and/or the data store 450.

In the example of FIG. 4, the second parasitic capacitance determination circuitry 455 determines a first parasitic impedance ($Z_{CE1}$), a second parasitic impedance ($Z_{CE2}$), a third parasitic impedance ($Z_{CE3}$), a fourth parasitic impedance ($Z_{CE4}$), a fifth parasitic impedance ($Z_{CE12}$), a sixth parasitic impedance ($Z_{CE13}$), a seventh parasitic impedance ($Z_{CE14}$), an eighth parasitic impedance ($Z_{CE23}$), a ninth parasitic impedance ($Z_{CE24}$), and a tenth parasitic impedance ($Z_{CE34}$).

The first parasitic impedance ($Z_{CE1}$) represents the first parasitic capacitance 205. The second parasitic impedance ($Z_{CE2}$) represents the second parasitic capacitance 210. The third parasitic impedance ($Z_{CE3}$) represents the third parasitic capacitance 215. The fourth parasitic impedance ($Z_{CE4}$) represents the fourth parasitic capacitance 220. The fifth parasitic impedance ($Z_{CE12}$) represents the first parasitic cross capacitance 225. The sixth parasitic impedance ($Z_{CE13}$) represents the second parasitic cross capacitance 230. The seventh parasitic impedance ($Z_{CE14}$) represents the third parasitic cross capacitance 235. The eighth parasitic impedance ($Z_{CE23}$) represents the fourth parasitic cross capacitance 240. The ninth parasitic impedance ($Z_{CE24}$) represents the fifth parasitic cross capacitance 245. The tenth parasitic impedance ($Z_{CE34}$) represents the first parasitic cross capacitance 250.

In some examples, the second parasitic capacitance determination circuitry 455 solves a system of current equations, which include the parasitic impedance values, to determine each of the parasitic impedance values. In such examples, the second parasitic capacitance determination circuitry 455 uses electrode voltages and currents from a plurality of configurations of the measurement circuitry 120. Each of the configurations of the measurement circuitry 120 represent a different configuration of the first multiplexer 308. In the example of FIG. 4, a first configuration of the measurement circuitry 120 corresponds to the first multiplexer 308 supplying the excitation currents to the impedance circuitries 310 and 312, a second configuration corresponds to the first multiplexer 308 supplying the excitation currents to the impedance circuitries 312 and 314, and a third configuration corresponds to the first multiplexer 308 supplying the excitation currents to the impedance circuitries 314 and 316.

While in each configuration, the calibration circuitry 320 determines electrode voltages and currents for each of the electrodes 140-170 using the determination circuitries 430-445. The calibration circuitry 320 stores the electrode voltages and currents for each of the configurations in the data store 450. The second parasitic capacitance determination circuitry 455 uses the stored electrode voltages and currents and Kirchhoff's current law to determine the parasitic impedances of the parasitic capacitances 205-250.

In an example operation, Equations (8)-(11), below, represent summing all paths of current in the electrode network 110 of FIGS. 1 and 2. In such an operation, the second parasitic capacitance determination circuitry 455 creates a plurality of instances of the Equations (8)-(11) using different configurations of the measurement circuitry 120. The second parasitic capacitance determination circuitry 455 uses an instance of the series of Equations (8)-(11), below, for each of configuration of the measurement circuitry 120. Each instance of the series of Equations (8)-(11), below, includes the electrode voltages and currents determined by the circuitries 430-445. The second parasitic capacitance determination circuitry 455 solves the plurality of sets of the Equations (8)-(11) for the parasitic impedances. In some examples, the second parasitic capacitance determination circuitry 455 uses four configurations of the measurement circuitry 120 to create four sets of the Equations (8)-(11), below, to generate sixteen total equations. In such examples, the second parasitic capacitance determination circuitry 455 solves the four sets of Equations (8)-(11) for the parasitic impedances. Such example operations to determine the parasitic capacitances 205-250 are described in FIGS. 5A and 5B, below.

$$I_1 = \frac{V_{E1}}{Z_{CE1}} + \frac{V_{E1} - V_{E2}}{Z_{CE12}} + \frac{V_{E1} - V_{E3}}{Z_{CE13}} + \frac{V_{E1} - V_{E4}}{Z_{CE14}}, \quad \text{Equation (8)}$$

$$I_2 = \frac{V_{E2}}{Z_{CE2}} + \frac{V_{E2} - V_{E1}}{Z_{CE12}} + \frac{V_{E2} - V_{E3}}{Z_{CE23}} + \frac{V_{E2} - V_{E4}}{Z_{CE24}}, \quad \text{Equation (9)}$$

$$I_3 = \frac{V_{E3}}{Z_{CE3}} + \frac{V_{E3} - V_{E1}}{Z_{CE13}} + \frac{V_{E3} - V_{E2}}{Z_{CE23}} + \frac{V_{E3} - V_{E4}}{Z_{CE34}}, \quad \text{Equation (10)}$$

$$I_4 = \frac{V_{E4}}{Z_{CE4}} + \frac{V_{E4} - V_{E1}}{Z_{CE14}} + \frac{V_{E4} - V_{E2}}{Z_{CE24}} + \frac{V_{E4} - V_{E3}}{Z_{CE34}}, \quad \text{Equation (11)}$$

In other examples, the second parasitic capacitance determination circuitry 455 uses effective capacitances of the parasitic capacitances 205-250 coupled to each of the electrodes 140-170 to determine approximate values of the parasitic capacitances 205-250. In such examples, the second parasitic capacitance determination circuitry 455 determines a first effective capacitance ($C_{E1\_EFF}$), a second effective capacitance ($C_{E2\_EFF}$), a third effective capacitance ($C_{E3\_EFF}$), and a fourth effective capacitance ($C_{E4\_EFF}$). The effective capacitances represent the combination of the parasitic capacitances 205-250 coupled to each of the electrodes 140-170. The second parasitic capacitance determination circuitry 455 determines each of the effective capacitances by dividing an electrode voltage, determined by one of the voltage determination circuitries 440 or 445, by an electrode current, determined by one of the current determination circuitries 430 or 435.

The first effective capacitance is a combination of the parasitic capacitances 205-235 coupled to the first electrode 140. The first effective capacitance is approximately equal to a parallel combination of the first parasitic capacitance 205, a series combination of the second parasitic capacitance 210 and the first parasitic cross capacitance 225, a series combination of the third parasitic capacitance 215 and the second parasitic cross capacitance 230, and a series combination of the fourth parasitic capacitance 220 and the third parasitic cross capacitance 235. The first effective capacitance may be determined using Equation (12), below.

$$C_{E1\_EFF} = C_{E1} + \frac{C_{E12} * C_{E2}}{C_{E12} + C_{E2}} + \frac{C_{E13} * C_{E3}}{C_{E13} + C_{E3}} + \frac{C_{E14} * C_{E4}}{C_{E14} + C_{E4}}, \quad \text{Equation (12)}$$

The second effective capacitance is a combination of the parasitic capacitances 205-225, 240, and 245 coupled to the second electrode 150. The second effective capacitance is approximately equal to a parallel combination of the second parasitic capacitance 210, a series combination of the first parasitic capacitance 205 and the first parasitic cross capacitance 225, a series combination of the third parasitic capacitance 215 and the fourth parasitic cross capacitance 240, and a series combination of the fourth parasitic capacitance 220 and the fifth parasitic cross capacitance 245. The second effective capacitance may be determined using Equation (13), below.

$$C_{E2\_EFF} = C_{E2} + \frac{C_{E12} * C_{E1}}{C_{E12} + C_{E1}} + \frac{C_{E23} * C_{E3}}{C_{E23} + C_{E3}} + \frac{C_{E24} * C_{E4}}{C_{E24} + C_{E4}}, \quad \text{Equation (13)}$$

The third effective capacitance is a combination of the parasitic capacitances 205-220, 230, 240, and 250 coupled to the third electrode 160. The third effective capacitance is approximately equal to a parallel combination of the third parasitic capacitance 215, a series combination of the first parasitic capacitance 205 and the second parasitic cross capacitance 230, a series combination of the second parasitic capacitance 210 and the fourth parasitic cross capacitance 240, and a series combination of the fourth parasitic capacitance 220 and the sixth parasitic cross capacitance 250. The third effective capacitance may be determined using Equation (14), below.

$$C_{E3\_EFF} = C_{E3} + \frac{C_{E13} * C_{E1}}{C_{E13} + C_{E1}} + \frac{C_{E23} * C_{E2}}{C_{E23} + C_{E2}} + \frac{C_{E34} * C_{E4}}{C_{E34} + C_{E4}}, \quad \text{Equation (14)}$$

The fourth effective capacitance is a combination of the parasitic capacitances 205-220, 235, 245, and 250 coupled to the fourth electrode 170. The fourth effective capacitance is approximately equal to a parallel combination of the fourth parasitic capacitance 220, a series combination of the first parasitic capacitance 205 and the third parasitic cross capacitance 235, a series combination of the second parasitic capacitance 210 and the fifth parasitic cross capacitance 245, and a series combination of the third parasitic capacitance 215 and the sixth parasitic cross capacitance 250. The fourth effective capacitance may be determined using Equation (15), below.

$$C_{E4\_EFF} = C_{E4} + \frac{C_{E14} * C_{E1}}{C_{E14} + C_{E1}} + \frac{C_{E24} * C_{E2}}{C_{E24} + C_{E2}} + \frac{C_{E34} * C_{E3}}{C_{E34} + C_{E3}}, \quad \text{Equation (15)}$$

In some examples, the second parasitic capacitance determination circuitry 455 determines the parasitic cross capacitances 225-250 using cross-talk measurements. Cross-talk measurements are ratio comparisons of voltages in response to an excitation current. In the example of FIG. 4, cross-talk measurements are comparisons of voltages of the excitation terminals of the impedance circuitries 310-316 in response to the first multiplexer 308 supplying one of the excitation currents to one of the impedance circuitries 310-316. The second parasitic capacitance determination circuitry 455 determines the parasitic cross capacitances 225-250 using three configurations of the measurement circuitry 120. In some examples, a first cross-talk configuration corresponds to the first multiplexer 308 supplying the first excitation current to the first impedance circuitry 310. In such examples, a second cross-talk configuration corresponds to the first multiplexer 308 supplying the first excitation current to the second impedance circuitry 312. In such examples, a third cross-talk configuration corresponds to the first multiplexer 308 supplying the first excitation current to the third impedance circuitry 314.

In the first cross-talk configuration, the second parasitic capacitance determination circuitry 455 determines the first parasitic cross capacitance ($C_{E12}$) 225 by setting a ratio of a voltage of the second excitation terminal ($V_{BIA\_E2}$) over a voltage of the first excitation terminal ($V_{BIA\_E1}$) equal to a ratio of the first parasitic cross capacitance 225 over a parallel combination of the parasitic capacitances (Cm) 332 and 340, when the desired impedance value are less than the parasitic capacitances 332 and 340, and the second effective capacitance ($C_{E2\_EEF}$). The parasitic capacitances 322 and 332 are approximately equal to one over the parasitic impedance ($Z_{CPN}$) determined by the first parasitic capacitance circuitry 425. The second parasitic capacitance determination circuitry 455 solves Equation (16), below, for the first parasitic cross capacitance 225.

$$\frac{V_{BIA\_E2}}{V_{BIA\_E1}} = \frac{C_{E12}}{2*C_{PIN} + C_{E2\_EFF}} \qquad \text{Equation (16)}$$

In the first cross-talk configuration, the second parasitic capacitance determination circuitry 455 determines the second parasitic cross capacitance ($C_{E13}$) 230 by setting a ratio of a voltage of the third excitation terminal ($V_{BIA\_E3}$) over the voltage of the first excitation terminal ($V_{BIA\_E1}$) equal to a ratio of the second parasitic cross capacitance 230 over a parallel combination of the parasitic capacitances ($C_{PIN}$) 322 and 342 and the third effective capacitance ($C_{E3\_EFF}$). The parasitic capacitances 322 and 342 are approximately equal to one over the parasitic impedance ($Z_{CPIN}$) determined by the first parasitic capacitance circuitry 425. The second parasitic capacitance determination circuitry 455 solves Equation (17), below, for the second parasitic cross capacitance 230.

$$\frac{V_{BIA\_E3}}{V_{BIA\_E1}} = \frac{C_{E13}}{2*C_{PIN} + C_{E3\_EFF}} \qquad \text{Equation (17)}$$

In the first cross-talk configuration, the second parasitic capacitance determination circuitry 455 determines the third parasitic cross capacitance ($C_{E14}$) 235 by setting a ratio of a voltage of the fourth excitation terminal ($V_{BIA\_E4}$) over the voltage of the first excitation terminal ($V_{BIA\_E1}$) equal to a ratio of the third parasitic cross capacitance 235 over a parallel combination of the parasitic capacitances ($C_{PIN}$) 322 and 352 and the fourth effective capacitance ($C_{E4\_EFF}$). The parasitic capacitances 322 and 352 are approximately equal to one over the parasitic impedance ($Z_{CPIN}$) determined by the first parasitic capacitance circuitry 425. The second parasitic capacitance determination circuitry 455 solves Equation (18), below, for the third parasitic cross capacitance 235.

$$\frac{V_{BIA\_E4}}{V_{BIA\_E1}} = \frac{C_{E14}}{2*C_{PIN} + C_{E4\_EFF}} \qquad \text{Equation (18)}$$

In the second cross-talk configuration, the second parasitic capacitance determination circuitry 455 determines the fourth parasitic cross capacitance ($C_{E23}$) 240 by setting a ratio of a voltage of the third excitation terminal ($V_{BIA\_E3}$) over the voltage of the second excitation terminal ($V_{BIA\_E2}$) equal to a ratio of the fourth parasitic cross capacitance 240 over a parallel combination of the parasitic capacitances (CNN) 332 and 342 and the third effective capacitance ($C_{E3\_EFF}$). The parasitic capacitances 332 and 342 are approximately equal to one over the parasitic impedance ($Z_{CPIN}$) determined by the first parasitic capacitance circuitry 425. The second parasitic capacitance determination circuitry 455 solves Equation (19), below, for the fourth parasitic cross capacitance 240.

$$\frac{V_{BIA\_E3}}{V_{BIA\_E2}} = \frac{C_{E23}}{2*C_{PIN} + C_{E3\_EFF}} \qquad \text{Equation (19)}$$

In the second cross-talk configuration, the second parasitic capacitance determination circuitry 455 determines the fifth parasitic cross capacitance ($C_{E24}$) 245 by setting a ratio of a voltage of the fourth excitation terminal ($V_{BIA\_E4}$) over the voltage of the second excitation terminal ($V_{BIA\_E2}$) equal to a ratio of the fifth parasitic cross capacitance 245 over a parallel combination of the parasitic capacitances ($C_{PIN}$) 332 and 352 and the fourth effective capacitance ($C_{E4\_EFF}$). The parasitic capacitances 332 and 352 are approximately equal to one over the parasitic impedance ($Z_{CPIN}$) determined by the first parasitic capacitance circuitry 425. The second parasitic capacitance determination circuitry 455 solves Equation (20), below, for the fifth parasitic cross capacitance 245.

$$\frac{V_{BIA\_E4}}{V_{BIA\_E2}} = \frac{C_{E24}}{2*C_{PIN} + C_{E4\_EFF}} \qquad \text{Equation (20)}$$

In the third cross-talk configuration, the second parasitic capacitance determination circuitry 455 determines the sixth parasitic cross capacitance ($C_{E34}$) 250 by setting a ratio of a voltage of the fourth excitation terminal ($V_{BIA\_E4}$) over the voltage of the third excitation terminal ($V_{BIA\_E2}$) equal to a ratio of the sixth parasitic cross capacitance 250 over a parallel combination of the parasitic capacitances ($C_{PIN}$) 342 and 352 and the fourth effective capacitance ($C_{E4\_EFF}$). The parasitic capacitances 342 and 352 are approximately equal to one over the parasitic impedance ($Z_{CPIN}$) determined by the first parasitic capacitance circuitry 425. The second parasitic capacitance determination circuitry 455 solves Equation (21), below, for the sixth parasitic cross capacitance 250.

$$\frac{V_{BIA\_E4}}{V_{BIA\_E3}} = \frac{C_{E34}}{2*C_{PIN} + C_{E4\_EFF}} \qquad \text{Equation (21)}$$

Advantageously, the second parasitic capacitance determination circuitry 455 may use the cross-talk measurements and Equations (16)-(21), above, to determine the parasitic cross capacitances 225-250. The second parasitic capacitance determination circuitry 455 determines the parasitic capacitances 205-220 using the determined effective capacitances, the determined parasitic cross capacitances 225-250, and the Equations (12)-(15), above.

In an example operation, the second parasitic capacitance determination circuitry 455 solves Equation (12), above, for the first parasitic capacitance 205. When solving for the first parasitic capacitance 205, the second parasitic capacitance determination circuitry 455 may use the second, third, and fourth effective capacitances as approximations of the parasitic capacitances 210-220.

In the example operation, the second parasitic capacitance determination circuitry 455 solves Equation (13), above, for the second parasitic capacitance 210. When solving for the second parasitic capacitance 210, the second parasitic capacitance determination circuitry 455 uses the first parasitic capacitance 205 determined using Equation (12) and may use the third and fourth effective capacitances as approximations of the parasitic capacitances 215 and 220.

In the example operation, the second parasitic capacitance determination circuitry 455 solves Equation (14), above, for the third parasitic capacitance 215. When solving for the third parasitic capacitance 215, the second parasitic capacitance determination circuitry 455 uses the parasitic capacitances 205 and 210 determined using Equations (12) and (13), above, and may use the fourth effective capacitances as an approximation of the fourth parasitic capacitance 220.

In the example operation, the second parasitic capacitance determination circuitry 455 solves Equation (15), above, for the fourth parasitic capacitance 220. When solving for the fourth parasitic capacitance 220, the second parasitic capacitance determination circuitry 455 uses the parasitic capacitances 205-215 determined using Equations (12)-(14), above.

In the example operation, the second parasitic capacitance determination circuitry 455 may resolve Equations (12)-(15), above, for the parasitic capacitances 205-220 using the parasitic capacitances 205-215 determined from a previous use of the Equations (12)-(15), above. Advantageously, the second parasitic capacitance determination circuitry 455 may increase an accuracy of the determined parasitic capacitances 205-220 by resolving Equations (12)-(15) a plurality of times using previously determined values of the parasitic capacitances 205-220.

Example operations to determine the parasitic capacitances 205-250 using effective capacitances are described in FIGS. 6A-6C, below. In some examples, the second parasitic capacitance determination circuitry 455 is instantiated by processor circuitry executing second parasitic capacitance determination instructions and/or configured to perform operations such as those represented by the flowcharts of FIGS. 5A and 5B or 6A-6C.

The compensation circuitry 460 is coupled to the data store 450 and the second parasitic capacitance determination circuitry 455. The compensation circuitry 460 receives electrode voltage values and electrode current values from the data store 450. The compensation circuitry 460 receives values of the parasitic capacitances 205-250 from the second parasitic capacitance determination circuitry. The compensation circuitry 460 determines a supply current (Iz E). The supply current is the current supplied by the electrodes 140-170 to an object. In the example of FIG. 1, the compensation circuitry 460 determines the current being supplied to the body 130. In some examples, the compensation circuitry 460 uses Kirchhoff's current law to determine the supply current. In such examples, the compensation circuitry 460 sets the supply current equal to the electrode current minus possible paths of the supply current.

In an example operation, the first multiplexer 308 supplies the first excitation current to the third impedance circuitry 314. In such a configuration, a third supply current ($I_{ZE3}$), which is the current supplied by the third electrode 160 to the body 130, is approximately equal to the third electrode current ($I_3$) minus current supplied by a first path through the third parasitic capacitance 215, by a second path through the second parasitic cross capacitance 230, by a third path through the fourth parasitic cross capacitance 240, and a fourth path through the sixth parasitic cross capacitance 250. The first current determination circuitry 430 determines the third electrode current.

A current, through the first path, is approximately equal to the third electrode voltage ($V_{E3}$), determined by the first voltage determination circuitry 440, divided by the parasitic impedance ($Z_{CE3}$) of the third parasitic capacitance 215, determined by the second parasitic capacitance determination circuitry 455. A current, through the second path, is approximately equal to a division of a subtraction of the first electrode voltage ($V_{E1}$), determined by the second voltage determination circuitry 445, from the third electrode voltage ($V_{E3}$), by the sixth parasitic impedance ($Z_{CE13}$) of the second parasitic cross capacitance 230, determined by the second parasitic capacitance determination circuitry 455. A current, through the third path, is approximately equal to a division of a subtraction of the second electrode voltage ($V_{E2}$), determined by the second voltage determination circuitry 445, from the third electrode voltage ($V_{E3}$), by the eighth parasitic impedance ($Z_{CE23}$) of the fourth parasitic cross capacitance 240, determined by the second parasitic capacitance determination circuitry 455. A current, through the fourth path, is approximately equal to a division of a subtraction of the fourth electrode voltage ($V_{E4}$), determined by the second voltage determination circuitry 445, from the third electrode voltage ($V_{E3}$), by the tenth parasitic impedance ($Z_{CE34}$) of the sixth parasitic cross capacitance 250, determined by the second parasitic capacitance determination circuitry 455.

Equation (22), below, illustrates applying Kirchhoff's current law to the first path, the second path, the third path, and the fourth path, described above. In such an operation, the compensation circuitry 460 solves Equation (22), below, for the third supply current, which is more generally referred to as the supply current.

$$I_{ZE3} = I_3 - \frac{V_{E3}}{Z_{CE3}} - \left(\frac{V_{E3} - V_{E1}}{Z_{CE13}}\right) - \left(\frac{V_{E3} - V_{E2}}{Z_{CE23}}\right) - \left(\frac{V_{E3} - V_{E4}}{Z_{CE34}}\right),$$

Equation (22)

Alternatively, the compensation circuitry 460 may use another example operation of the measurement circuitry 120 to determine the current being supplied by the electrodes 140-170 in accordance with the teachings described herein. In some examples, the compensation circuitry 460 is instantiated by processor circuitry executing compensation instructions and/or configured to perform operations such as those represented by the flowcharts of FIGS. 5A-6C.

While an example manner of implementing the calibration circuitry 320 of FIG. 3 is illustrated in FIG. 4, one or more of the elements, processes, and/or devices illustrated in FIG. 4 may be combined, divided, re-arranged, omitted, eliminated, and/or implemented in any other way. Further, the circuitries 405-445, 455, and 460, and/or, more generally, the example calibration circuitry 320 of FIG. 3, may be implemented by hardware alone or by hardware in combination with software and/or firmware. Thus, for example, any of the circuitries 405-445, 455, and 460, and/or, more generally, the calibration circuitry 320, could be implemented by processor circuitry, analog circuit(s), digital circuit(s), logic circuit(s), programmable processor(s), programmable microcontroller(s), graphics processing unit(s) (GPU(s)), digital signal processor(s) (DSP(s)), application specific integrated circuit(s) (ASIC(s)), programmable logic device(s) (PLD(s)), and/or field programmable logic device(s) (FPLD(s)) such as Field Programmable Gate Arrays (FPGAs). Further still, the example calibration circuitry 320 of FIG. 3 may include one or more elements, processes, and/or devices in addition to, or instead of, those illustrated in FIG. 4, and/or may include more than one of any or all of the illustrated elements, processes and devices.

A flowchart representative of example machine readable instructions, which may be executed to configure processor circuitry to implement the calibration circuitry 320 of FIGS. 3 and 4, is shown in FIGS. 5A-6C. The machine readable instructions may be one or more executable programs or portion(s) of an executable program for execution by processor circuitry, such as the processor circuitry 712 shown in the example processor platform 700 described below in connection with FIG. 7 and/or the example processor circuitry described below in connection with FIGS. 8 and/or 9. The program may be embodied in software stored on one or more non-transitory computer readable storage media such as a compact disk (CD), a floppy disk, a hard disk drive (HDD), a solid-state drive (SSD), a digital versatile disk (DVD), a Blu-ray disk, a volatile memory (e.g., Random Access Memory (RAM) of any type, etc.), or a non-volatile memory (e.g., electrically erasable programmable read-only memory (EEPROM), FLASH memory, an HDD, an SSD, etc.) associated with processor circuitry located in one or more hardware devices, but the entire program and/or parts thereof could alternatively be executed by one or more hardware devices other than the processor circuitry and/or embodied in firmware or dedicated hardware.

The machine readable instructions may be distributed across multiple hardware devices and/or executed by two or more hardware devices (e.g., a server and a client hardware device). For example, the client hardware device may be implemented by an endpoint client hardware device (e.g., a hardware device associated with a user) or an intermediate client hardware device (e.g., a radio access network (RAN)) gateway that may facilitate communication between a server and an endpoint client hardware device). Similarly, the non-transitory computer readable storage media may include one or more mediums located in one or more hardware devices. Further, although the example program is described with reference to the flowchart illustrated in FIGS. 5A-6C, many other methods of implementing the example calibration circuitry 320 may alternatively be used. For example, the order of execution of the blocks may be changed, and/or some of the blocks described may be changed, eliminated, or combined.

Additionally or alternatively, any or all of the blocks may be implemented by one or more hardware circuits (e.g., processor circuitry, discrete and/or integrated analog and/or digital circuitry, an FPGA, an ASIC, a comparator, an operational-amplifier (op-amp), a logic circuit, etc.) structured to perform the corresponding operation without executing software or firmware. The processor circuitry may be distributed in different network locations and/or local to one or more hardware devices (e.g., a single-core processor (e.g., a single core central processor unit (CPU)), a multi-core processor (e.g., a multi-core CPU, an XPU, etc.) in a single machine, multiple processors distributed across multiple servers of a server rack, multiple processors distributed across one or more server racks, a CPU and/or a FPGA located in the same package (e.g., the same integrated circuit (IC) package or in two or more separate housings, etc.).

The machine readable instructions described herein may be stored in one or more of a compressed format, an encrypted format, a fragmented format, a compiled format, an executable format, a packaged format, etc. Machine readable instructions as described herein may be stored as data or a data structure (e.g., as portions of instructions, code, representations of code, etc.) that may be utilized to create, manufacture, and/or produce machine executable instructions. For example, the machine readable instructions may be fragmented and stored on one or more storage devices and/or computing devices (e.g., servers) located at the same or different locations of a network or collection of networks (e.g., in the cloud, in edge devices, etc.). The machine readable instructions may require one or more of installation, modification, adaptation, updating, combining, supplementing, configuring, decryption, decompression, unpacking, distribution, reassignment, compilation, etc., in order to make them directly readable, interpretable, and/or executable by a computing device and/or other machine. For example, the machine readable instructions may be stored in multiple parts, which are individually compressed, encrypted, and/or stored on separate computing devices, wherein the parts when decrypted, decompressed, and/or combined form a set of machine executable instructions that implement one or more operations that may together form a program such as that described herein.

In another example, the machine readable instructions may be stored in a state in which they may be read by processor circuitry, but require addition of a library (e.g., a dynamic link library (DLL)), a software development kit (SDK), an application programming interface (API), etc., in order to execute the machine readable instructions on a particular computing device or other device. In another example, the machine readable instructions may need to be configured (e.g., settings stored, data input, network addresses recorded, etc.) before the machine readable instructions and/or the corresponding program(s) can be executed in whole or in part. Thus, machine readable media, as used herein, may include machine readable instructions and/or program(s) regardless of the particular format or state of the machine readable instructions and/or program(s) when stored or otherwise at rest or in transit.

The machine readable instructions described herein can be represented by any past, present, or future instruction language, scripting language, programming language, etc. For example, the machine-readable instructions may be represented using any of the following languages: C, C++, Java, C #, Perl, Python, JavaScript, HyperText Markup Language (HTML), Structured Query Language (SQL), Swift, etc.

As mentioned above, the example operations of FIGS. 5A-6C may be implemented using executable instructions (e.g., computer and/or machine readable instructions) stored on one or more non-transitory computer and/or machine readable media such as optical storage devices, magnetic storage devices, an HDD, a flash memory, a read-only memory (ROM), a CD, a DVD, a cache, a RAM of any type, a register, and/or any other storage device or storage disk in which information is stored for any duration (e.g., for extended time periods, permanently, for brief instances, for temporarily buffering, and/or for caching of the information).

As used herein, the terms non-transitory computer readable medium, non-transitory computer readable storage medium, non-transitory machine readable medium, and non-transitory machine readable storage medium are expressly defined to include any type of computer readable storage device and/or storage disk and to exclude propagating signals and to exclude transmission media. As used herein, the terms "computer readable storage device" and "machine readable storage device" are defined to include any physical (mechanical and/or electrical) structure to store information, but to exclude propagating signals and to exclude transmission media. Examples of computer readable storage devices and machine readable storage devices include random access memory of any type, read only memory of any type, solid state memory, flash memory, optical discs, magnetic disks, disk drives, and/or redundant array of independent disks (RAID) systems. As used herein, the term "device" refers to physical structure such as mechanical and/or electrical equipment, hardware, and/or circuitry that may or may not be configured by computer readable instructions, machine readable instructions, etc., and/or manufactured to execute computer readable instructions, machine readable instructions, etc.

"Including" and "comprising" (and all forms and tenses thereof) are used herein to be open ended terms. Thus, whenever a claim employs any form of "include" or "comprise" (e.g., comprises, includes, comprising, including, having, etc.) as a preamble or within a claim recitation of any kind, it is to be understood that additional elements, terms, etc., may be present without falling outside the scope of the corresponding claim or recitation. As used herein, when the phrase "at least" is used as the transition term in, for example, a preamble of a claim, it is open-ended in the same manner as the term "comprising" and "including" are open ended. The term "and/or" when used, for example, in a form such as A, B, and/or C refers to any combination or subset of A, B, C such as (1) A alone, (2) B alone, (3) C alone, (4) A with B, (5) A with C, (6) B with C, or (7) A with B and with C.

As used herein in the context of describing structures, components, items, objects and/or things, the phrase "at least one of A and B" is intended to refer to implementations including any of (1) at least one A, (2) at least one B, or (3) at least one A and at least one B. Similarly, as used herein in the context of describing structures, components, items, objects and/or things, the phrase "at least one of A or B" is intended to refer to implementations including any of (1) at least one A, (2) at least one B, or (3) at least one A and at least one B. As used herein in the context of describing the performance or execution of processes, instructions, actions, activities and/or steps, the phrase "at least one of A and B" is intended to refer to implementations including any of (1) at least one A, (2) at least one B, or (3) at least one A and at least one B. Similarly, as used herein in the context of describing the performance or execution of processes, instructions, actions, activities and/or steps, the phrase "at least one of A or B" is intended to refer to implementations including any of (1) at least one A, (2) at least one B, or (3) at least one A and at least one B.

As used herein, singular references (e.g., "a", "an", "first", "second", etc.) do not exclude a plurality. The term "a" or "an" object, as used herein, refers to one or more of that object. The terms "a" (or "an"), "one or more", and "at least one" are used interchangeably herein. Furthermore, although individually listed, a plurality of means, elements or method actions may be implemented by, e.g., the same entity or object. Additionally, although individual features may be included in different examples or claims, these may possibly be combined, and the inclusion in different examples or claims does not imply that a combination of features is not feasible and/or advantageous.

Figure 5A:
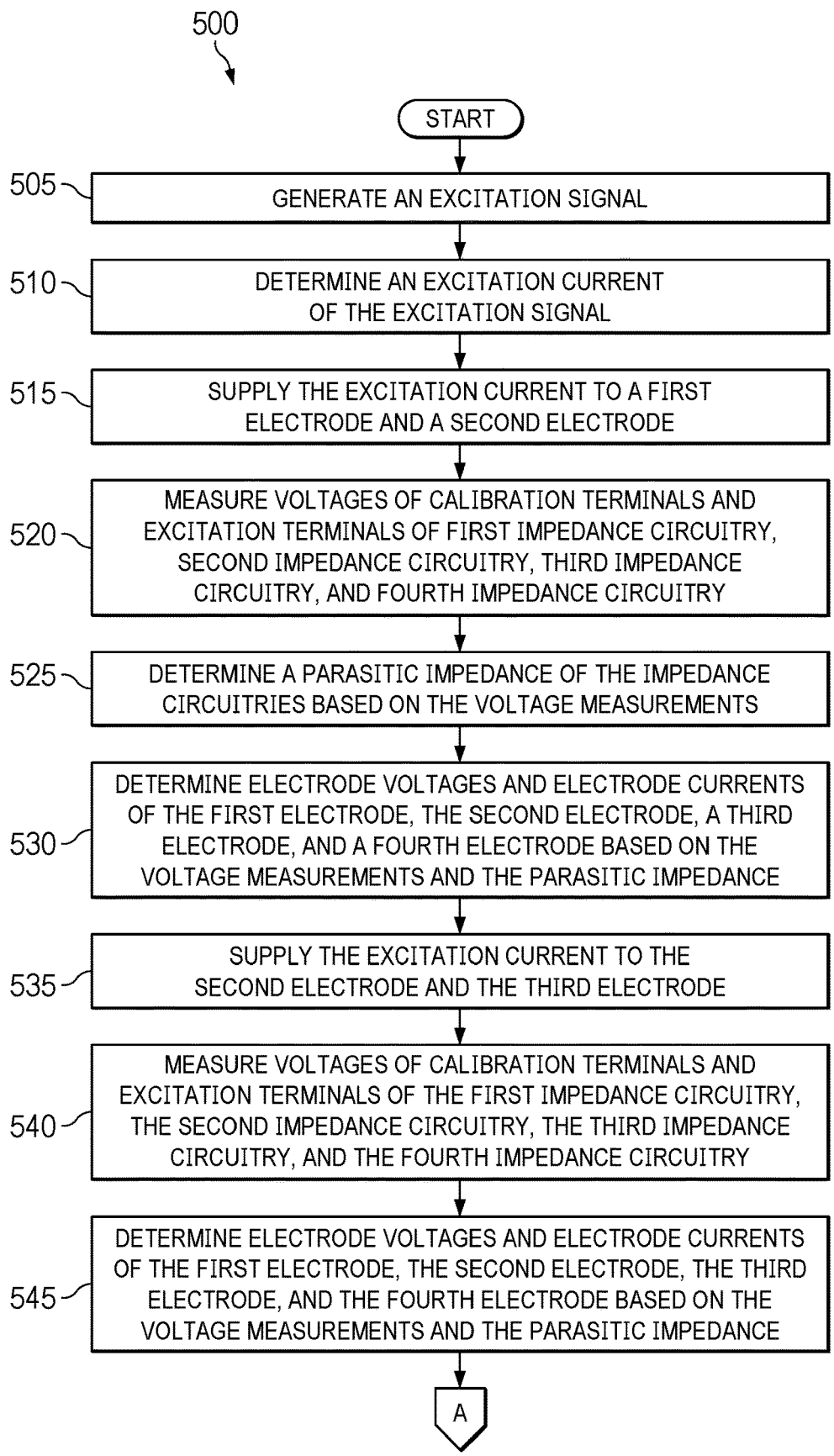
FIGS. 5A and 5B are a flowchart representative of an example process that may be performed using machine readable instructions that can be executed and/or performed using an example hardware implementation of the measurement circuitry of FIGS. 1 and 3 to determine the parasitic capacitances of FIG. 2.
Figure 5B:
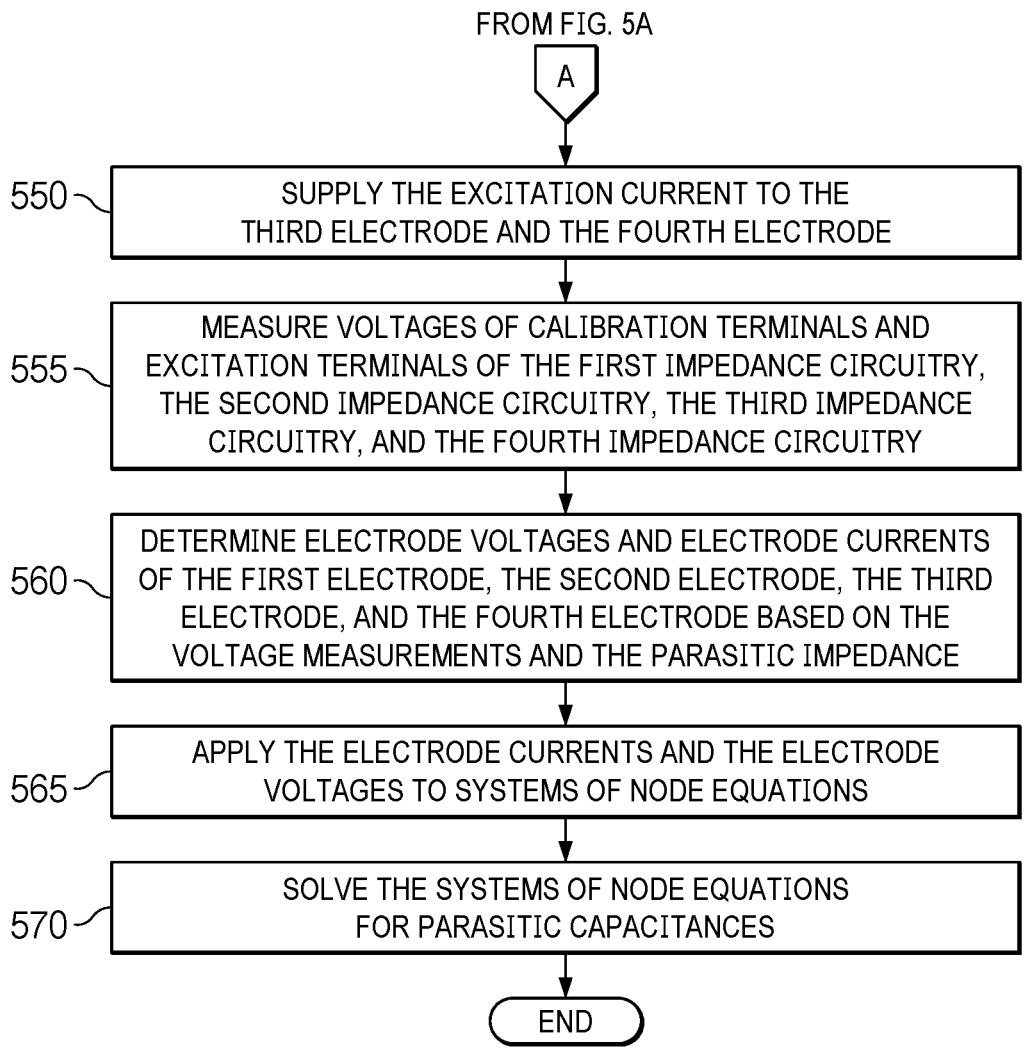

FIGS. 5A and 5B are a flowchart representative of an example process that may be performed using machine-readable instructions that can be executed and/or hardware configured to implement the measurement circuitry 120 of FIGS. 1 and 3 to determine the parasitic capacitances 205-250 of FIG. 2. The machine-readable instructions and/or operations 500 of FIGS. 5A and 5B begin at block 505, at which the transmitter 302 of FIG. 3 generates an excitation signal. (Block 505). In some examples, the transmitter 302 generates a sinusoidal signal as the excitation signal.

The current sense circuitries 405 and/or 410 of FIG. 4 determine an excitation current of the excitation signal. (Block 510). In some examples the current sense circuitries 405 and/or 410 use Equations (1) and/or (2), above, to determine excitation currents ($I_{RINT1}$ and/or $I_{RINT2}$).

The first multiplexer 308 of FIG. 3 supplies the excitation current to the first electrode 140 of FIGS. 1 and 2 and the second electrode 150 of FIGS. 1 and 2. (Block 515). In some examples, the multiplexer controller 420 of FIG. 4 controls the first multiplexer 308 to provide the first excitation current ($I_{INT1}$) to the first impedance circuitry 310 of FIG. 3 and the second excitation current ($I_{INT2}$) to the second impedance circuitry 312 of FIG. 3. In such examples, the impedance circuitries 310 and 312 supply the excitation currents to the electrodes 140 and 150.

The calibration circuitry 320 measures voltages of the calibration terminals ($V_{CAL}$) and the excitation terminals ($V_{BIA}$) of the first impedance circuitry 310, the second impedance circuitry 312, the third impedance circuitry 314 of FIG. 3, and the fourth impedance circuitry 316 of FIG. 3. (Block 520). In some examples, the second multiplexer 318 of FIG. 3 couples the excitation terminals and the calibration terminals of the impedance circuitries 310-316 to the measurement circuitry 415 of FIG. 4. In such examples, the measurement circuitry 415 may use sequencing to cause the multiplexer controller 420 to control the second multiplexer 318. In other examples, the measurement circuitry 415 may be directly coupled to the excitation terminals and the calibration terminals of the impedance circuitries 310-316.

The first parasitic capacitance determination circuitry 425 of FIG. 4 determines a parasitic impedance ($Z_{CPIN}$) of the impedance circuitries 310-316 based on the voltage measurements. (Block 525). In some examples, the first parasitic capacitance determination circuitry 425 solves Equation (3), above, for the parasitic impedance of the parasitic capacitances 322, 330, 332, 340, 342, 350, 352, and 360 of FIG. 3 of the impedance circuitries 310-316.

The determination circuitries 430-445 of FIG. 4 determine electrode voltages and electrode currents of the first electrode 140, the second electrode 150, the third electrode 160, and the fourth electrode 170 based on the voltage measurements and the parasitic impedance. (Block 530). In some examples, the first current determination circuitry 430 and the first voltage determination circuitry 440 determine electrode currents and electrode voltages of electrodes that are supplied the excitation current, such as the electrodes 140 and 150. For example, the circuitries 430 and 440 use Equations (4) and (6), above, to determine the excited electrode currents and the excited electrode voltages of the electrodes 140 and 150. In such examples, the second current determination circuitry 435 and the second voltage determination circuitry 445 determine electrode currents and electrode voltages of electrodes that are not supplied the excitation current, such as the electrodes 160 and 170. For example, the circuitries 435 and 445 use Equations (5) and (7), above, to determine the non-excited electrode currents and the non-excited electrode voltages of the electrodes 160 and 170.

The first multiplexer 308 supplies the excitation current to the second electrode 150 and the third electrode 160. (Block 535). In some examples, the multiplexer controller 420 controls the first multiplexer 308 to provide the first excitation current ($I_{RNT1}$) to the second impedance circuitry 312 and the second excitation current ($I_{RINT2}$) to the third impedance circuitry 314. In such examples, the impedance circuitries 312 and 314 supply the excitation currents to the electrodes 150 and 160.

The calibration circuitry 320 measures voltages of the calibration terminals ($V_{CAL}$) and the excitation terminals ($V_{BIA}$) of the first impedance circuitry 310, the second impedance circuitry 312, the third impedance circuitry 314, and the fourth impedance circuitry 316. (Block 540). In some examples, the second multiplexer 318 couples the excitation terminals and the calibration terminals of the impedance circuitries 310-316 to the measurement circuitry 415. In such examples, the measurement circuitry 415 may use sequencing to cause the multiplexer controller 420 to configure the second multiplexer 318. In other examples, the measurement circuitry 415 may be directly coupled to the excitation terminals and the calibration terminals of the impedance circuitries 310-316.

The determination circuitries 430-445 determine electrode voltages and electrode currents of the first electrode 140, the second electrode 150, the third electrode 160, and the fourth electrode 170 based on the voltage measurements and the parasitic impedance. (Block 545). In some examples, the first current determination circuitry 430 and the first voltage determination circuitry 440 determine electrode currents and electrode voltages of electrodes that are supplied the excitation current, such as the electrodes 150 and 160. For example, the circuitries 430 and 440 use Equations (4) and (6), above, to determine the excited electrode currents and the excited electrode voltages of the electrodes 150 and 160. In such examples, the second current determination circuitry 435 and the second voltage determination circuitry 445 determine electrode currents and electrode voltages of electrodes that are not supplied the excitation current, such as the electrodes 150 and 160. For example, the circuitries 435 and 445 use Equations (5) and (7), above, to determine the non-excited electrode currents and the non-excited electrode voltages of the electrodes 140 and 170.

Turning to FIG. 5B, the first multiplexer 308 supplies the excitation current to the third electrode 160 and the fourth electrode 170. (Block 550). In some examples, the multiplexer controller 420 controls the first multiplexer 308 to provide the first excitation current ($I_{RINT1}$) to the third impedance circuitry 314 and the second excitation current ($I_{RINT2}$) to the fourth impedance circuitry 316. In such examples, the impedance circuitries 314 and 316 supply the excitation currents to the electrodes 160 and 170.

The calibration circuitry 320 measures voltages of the calibration terminals ($V_{CAL}$) and the excitation terminals ($V_{BIA}$) of the first impedance circuitry 310, the second impedance circuitry 312, the third impedance circuitry 314, and the fourth impedance circuitry 316. (Block 555). In some examples, the second multiplexer 318 couples the excitation terminals and the calibration terminals of the impedance circuitries 310-316 to the measurement circuitry 415. In such examples, the measurement circuitry 415 may use sequencing to cause the multiplexer controller 420 to control the second multiplexer 318. In other examples, the measurement circuitry 415 may be directly coupled to the excitation terminals and the calibration terminals of the impedance circuitries 310-316.

The determination circuitries 430-445 determine electrode voltages and electrode currents of the first electrode 140, the second electrode 150, the third electrode 160, and the fourth electrode 170 based on the voltage measurements and the parasitic impedance. (Block 560). In some examples, the first current determination circuitry 430 and the first voltage determination circuitry 440 determine electrode currents and electrode voltages of electrodes that are supplied the excitation current, such as the electrodes 160 and 170. For example, the circuitries 430 and 440 use Equations (4) and (6), above, to determine the excited electrode currents and the excited electrode voltages of the electrodes 160 and 170. In such examples, the second current determination circuitry 435 and the second voltage determination circuitry 445 determine electrode currents and electrode voltages of electrodes that are not supplied the excitation current, such as the electrodes 140 and 150. For example, the circuitries 435 and 445 use Equations (5) and (7), above, to determine the non-excited electrode currents and the non-excited electrode voltages of the electrodes 140 and 170.

The second parasitic capacitance determination circuitry 455 of FIG. 4 applies the electrode current values and the electrode voltage values to systems of equations. (Block 565). In some examples, the second parasitic capacitance determination circuitry 455 applies electrode currents and electrode voltages from the determination circuitries 430-445 to the system of Equations (8)-(11), above. In such examples, the second parasitic capacitance determination circuitry 455 uses an instance of the system of Equations (8)-(11), above, for each configuration of the measurement circuitry 120, such as each of the Blocks 515, 535, and 550 corresponding to three configurations. For example, the second parasitic capacitance determination circuitry 455 applies the electrode currents and electrode voltages from Blocks 515, 535, and 550 to the Equations (8)-(11) to generate a system of twelve equations.

The second parasitic capacitance determination circuitry 455 solves the systems of equations for parasitic capacitances 205-250. (Block 570). In some examples, the second parasitic capacitance determination circuitry 455 solves the twelve equations for the parasitic capacitances 205-250. The control proceeds to end.

Although example processes are described with reference to the flowchart illustrated in FIGS. 5A and 5B, many other methods of determining parasitic capacitances may alternatively be used in accordance with the teachings of this description. For example, the order of execution of the blocks may be changed, and/or some of the blocks described may be changed, eliminated, or combined. Similarly, additional operations may be included in the manufacturing process before, in between, or after the blocks shown in the illustrated examples.

Figure 6B:
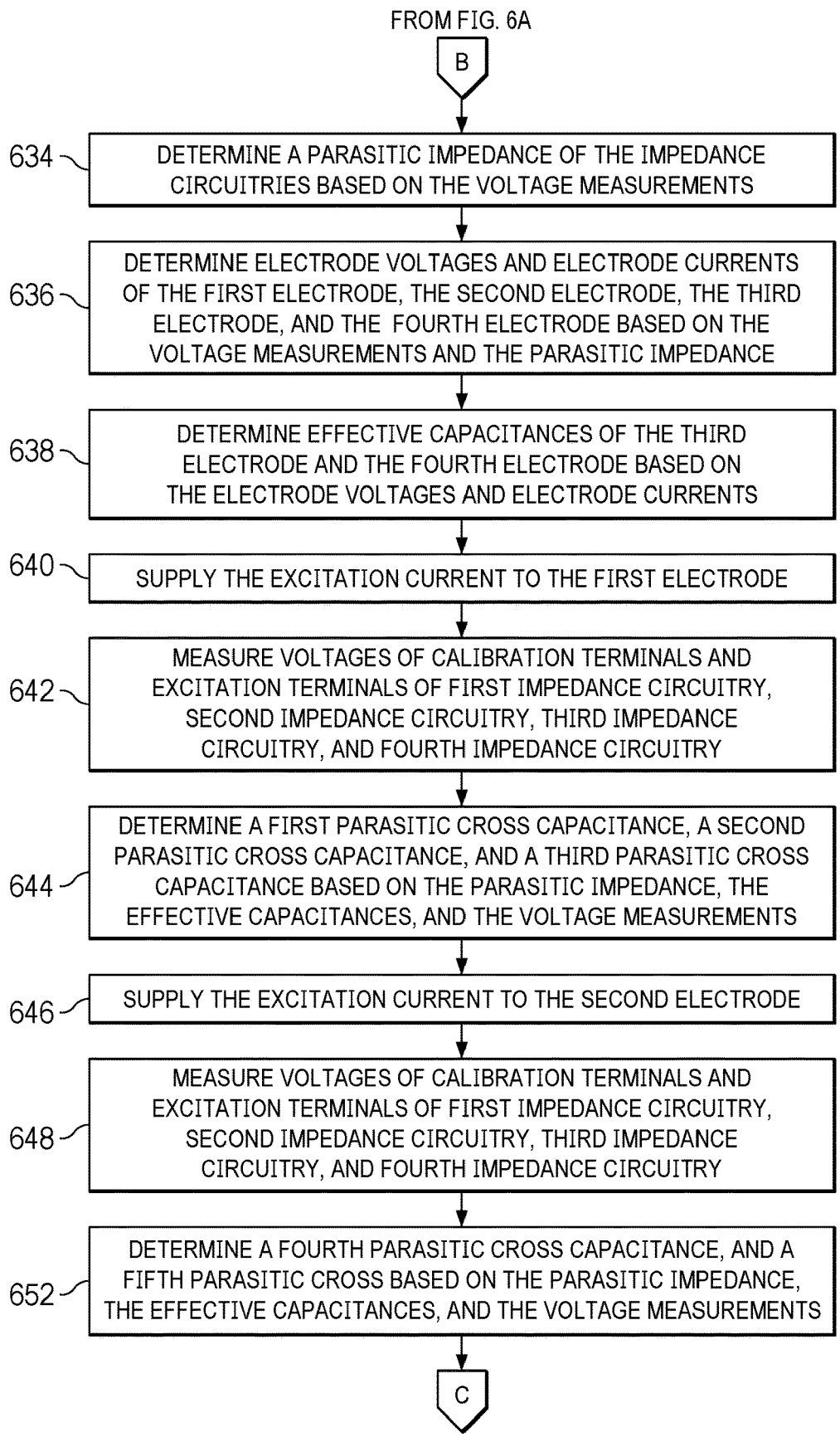
Figure 6C:
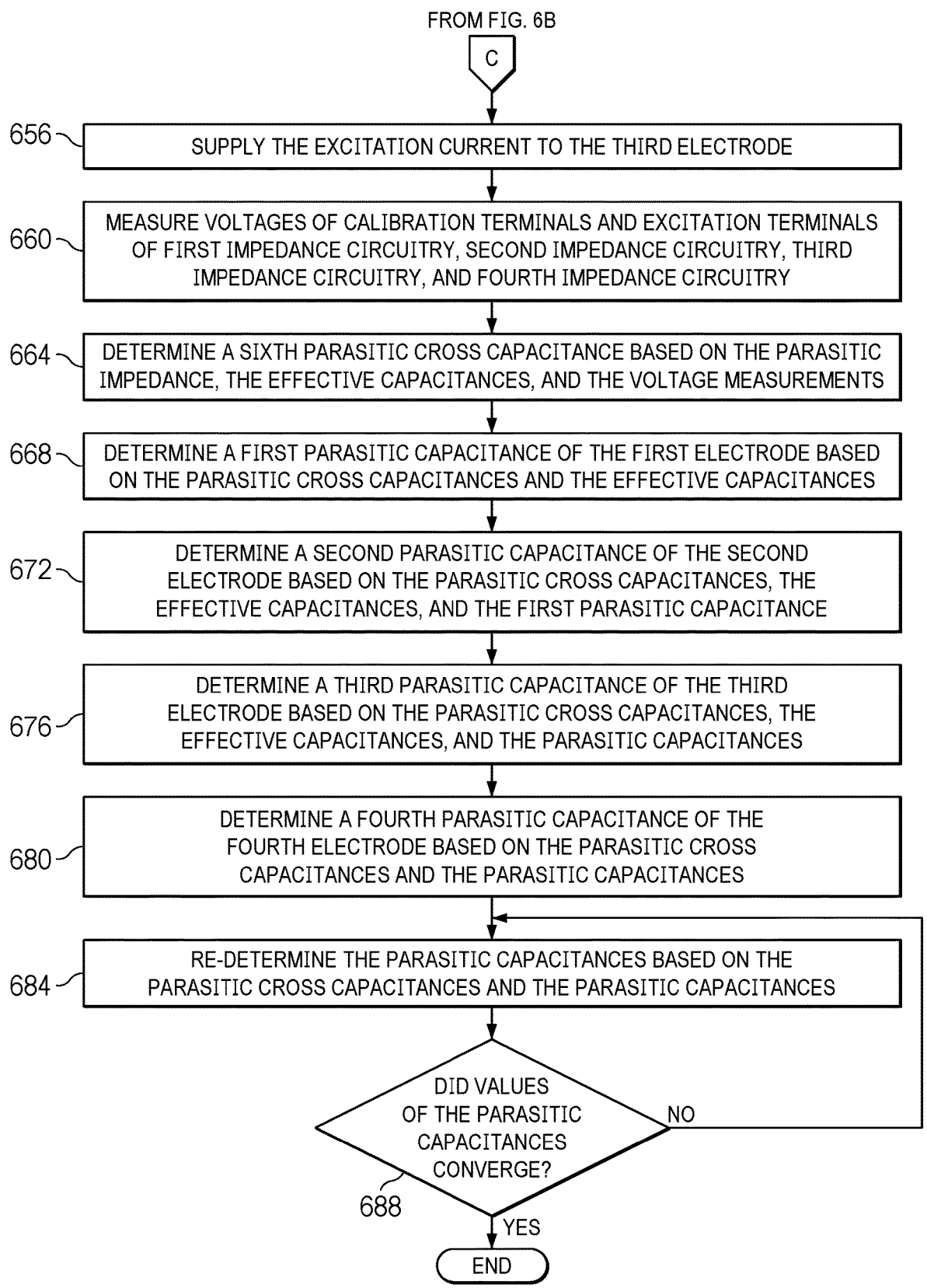

FIGS. 6A, 6B, and 6C are a flowchart representative of an example process that may be performed using machine-readable instructions that can be executed and/or hardware configured to implement the measurement circuitry 120 of FIGS. 1 and 3 to determine the parasitic capacitances 205-250 of FIG. 2. The machine-readable instructions and/or operations 600 of FIGS. 6A, 6B, and 6C begin at block 604, at which the transmitter 302 of FIG. 3 generates an excitation signal. (Block 604). In some examples, the transmitter 302 generates a sinusoidal signal as the excitation signal.

The current sense circuitries 405 and/or 410 of FIG. 4 determine an excitation current of the excitation signal. (Block 608). In some examples the current sense circuitries 405 and/or 410 use Equations (1) and/or (2), above, to determine excitation currents ($I_{RINT1}$ and/or $I_{RINT2}$).

The first multiplexer 308 of FIG. 3 supplies the excitation current to the first electrode 140 of FIGS. 1 and 2 and the second electrode 150 of FIGS. 1 and 2. (Block 612). In some examples, the multiplexer controller 420 of FIG. 4 controls the first multiplexer 308 to provide the first excitation current ($I_{RINT1}$) to the first impedance circuitry 310 of FIG. 3 and the second excitation current ($I_{RINT2}$) to the second impedance circuitry 312 of FIG. 3. In such examples, the impedance circuitries 310 and 312 supply the excitation currents to the electrodes 140 and 150.

The calibration circuitry 320 measures voltages of the calibration terminals ($V_{CAL}$) and the excitation terminals ($V_{BIA}$) of the first impedance circuitry 310, the second impedance circuitry 312, the third impedance circuitry 314 of FIG. 3, and the fourth impedance circuitry 316 of FIG. 3. (Block 616). In some examples, the second multiplexer 318 of FIG. 3 couples the excitation terminals and the calibration terminals of the impedance circuitries 310-316 to the measurement circuitry 415 of FIG. 4. In such examples, the measurement circuitry 415 may use sequencing to cause the multiplexer controller 420 to control the second multiplexer 318. In other examples, the measurement circuitry 415 may be directly coupled to the excitation terminals and the calibration terminals of the impedance circuitries 310-316.

The first parasitic capacitance determination circuitry 425 of FIG. 4 determines a parasitic impedance ($Z_{CPIN}$) of the impedance circuitries 310-316 based on the voltage measurements. (Block 620). In some examples, the first parasitic capacitance determination circuitry 425 solves Equation (3), above, for the parasitic impedance of the parasitic capacitances 322, 330, 332, 340, 342, 350, 352, and 360 of FIG. 3 of the impedance circuitries 310-316.

The determination circuitries 430-445 of FIG. 4 determine electrode voltages and electrode currents of the first electrode 140, the second electrode 150, the third electrode 160, and the fourth electrode 170 based on the voltage measurements and the parasitic impedance. (Block 624). In some examples, the first current determination circuitry 430 and the first voltage determination circuitry 440 determine electrode currents and electrode voltages of electrodes that are supplied the excitation current, such as the electrodes 140 and 150. For example, the circuitries 430 and 440 use Equations (4) and (6), above, to determine the excited electrode currents and the excited electrode voltages of the electrodes 140 and 150. In such examples, the second current determination circuitry 435 and the second voltage determination circuitry 445 determine electrode currents and electrode voltages of electrodes that are not supplied the excitation current, such as the electrodes 160 and 170. For example, the circuitries 435 and 445 use Equations (5) and (7), above, to determine the non-excited electrode currents and the non-excited electrode voltages of the electrodes 160 and 170.

The second parasitic capacitance determination circuitry 455 of FIG. 4 determines effective capacitances ($C_{EFF}$) of the first electrode 140 and the second electrode 150 based on the electrode voltages and electrode currents. (Block 628). In some examples, the second parasitic capacitance determination circuitry 455 determines the effective capacitances of the electrodes 140-170 by dividing an electrode voltage by an electrode current to determine an effective impedance. In such examples, the effective capacitance is approximately one over the effective impedance.

The first multiplexer 308 supplies the excitation current to the third electrode 160 of and the fourth electrode 170. (Block 630). In some examples, the multiplexer controller 420 controls the first multiplexer 308 to provide the first excitation current to the third impedance circuitry 314 and the second excitation current to the fourth impedance circuitry 316. In such examples, the impedance circuitries 314 and 316 supply the excitation currents to the electrodes 160 and 170.

The calibration circuitry 320 measures voltages of the calibration terminals ($V_{CAL}$) and the excitation terminals ($V_{BIA}$) of the first impedance circuitry 310, the second impedance circuitry 312, the third impedance circuitry 314, and the fourth impedance circuitry 316. (Block 632). In some examples, the second multiplexer 318 couples the excitation terminals and the calibration terminals of the impedance circuitries 310-316 to the measurement circuitry 415. In such examples, the measurement circuitry 415 may use sequencing to cause the multiplexer controller 420 to control the second multiplexer 318. In other examples, the measurement circuitry 415 may be directly coupled to the excitation terminals and the calibration terminals of the impedance circuitries 310-316.

Turning now to FIG. 6B, the first parasitic capacitance determination circuitry 425 determines a parasitic impedance ($Z_{CPIN}$) of the impedance circuitries 310-316 based on the voltage measurements. (Block 634). In some examples, the first parasitic capacitance determination circuitry 425 solves Equation (3), above, for the parasitic impedance of the parasitic capacitances 322, 330, 332, 340, 342, 350, 352, and 360 of the impedance circuitries 310-316.

The determination circuitries 430-445 determine electrode voltages and electrode currents of the first electrode 140, the second electrode 150, the third electrode 160, and the fourth electrode 170 based on the voltage measurements and the parasitic impedance. (Block 636). In some examples, the first current determination circuitry 430 and the first voltage determination circuitry 440 determine electrode currents and electrode voltages of electrodes that are supplied the excitation current, such as the electrodes 160 and 170. For example, the circuitries 430 and 440 use Equations (4) and (6), above, to determine the excited electrode currents and the excited electrode voltages of the electrodes 160 and 170. In such examples, the second current determination circuitry 435 and the second voltage determination circuitry 445 determine electrode currents and electrode voltages of electrodes that are not supplied the excitation current, such as the electrodes 140 and 150. For example, the circuitries 435 and 445 use Equations (5) and (7), above, to determine the non-excited electrode currents and the non-excited electrode voltages of the electrodes 140 and 150.

The second parasitic capacitance determination circuitry 455 determines effective capacitances ($C_{EFF}$) of the third electrode 160 and the fourth electrode 170 based on the electrode voltages and electrode currents. (Block 638). In some examples, the second parasitic capacitance determination circuitry 455 determines the effective capacitances of the electrodes 140-170 by dividing an electrode voltage by an electrode current to determine an effective impedance. In such examples, the effective capacitance is approximately one over the effective impedance.

The first multiplexer 308 supplies the excitation current to the first electrode 140. (Block 640). In some examples, the multiplexer controller 420 controls the first multiplexer 308 to provide the first excitation current ($I_{RINT1}$) to the first impedance circuitry 310. In such examples, the first impedance circuitry 310 supplies the first excitation current to the first electrode 140.

The calibration circuitry 320 measures voltages of the calibration terminals ($V_{CAL}$) and the excitation terminals ($V_{BIA}$) of the first impedance circuitry 310, the second impedance circuitry 312, the third impedance circuitry 314, and the fourth impedance circuitry 316. (Block 642). In some examples, the second multiplexer 318 couples the excitation terminals and the calibration terminals of the impedance circuitries 310-316 to the measurement circuitry 415. In such examples, the measurement circuitry 415 may use sequencing to cause the multiplexer controller 420 to control the second multiplexer 318. In other examples, the measurement circuitry 415 may be directly coupled to the excitation terminals and the calibration terminals of the impedance circuitries 310-316.

The second parasitic capacitance determination circuitry 455 determines the first parasitic cross capacitance 225, the second parasitic cross capacitance 230, and the third parasitic cross capacitance 235 based on the parasitic impedance the effective capacitances and the voltage measurements. (Block 644). In some examples, the second parasitic capacitance determination circuitry 455 determines the parasitic cross capacitances 225-235 by solving Equations (16)-(18), above. In such examples, the operations of Blocks 640-644 may be referred to as cross-talk measurements.

The first multiplexer 308 supplies the excitation current to the second electrode 150. (Block 646). In some examples, the multiplexer controller 420 controls the first multiplexer 308 to provide the first excitation current ($I_{RINT1}$) to the second impedance circuitry 312. In such examples, the second impedance circuitry 312 supplies the first excitation current to the second electrode 150.

The calibration circuitry 320 measures voltages of the calibration terminals ($V_{CAL}$) and the excitation terminals ($V_{BIA}$) of the first impedance circuitry 310, the second impedance circuitry 312, the third impedance circuitry 314, and the fourth impedance circuitry 316. (Block 648). In some examples, the second multiplexer 318 couples the excitation terminals and the calibration terminals of the impedance circuitries 310-316 to the measurement circuitry 415. In such examples, the measurement circuitry 415 may use sequencing to cause the multiplexer controller 420 to control the second multiplexer 318. In other examples, the measurement circuitry 415 may be directly coupled to the excitation terminals and the calibration terminals of the impedance circuitries 310-316.

The second parasitic capacitance determination circuitry 455 determines the fourth parasitic cross capacitance 240 and the fifth parasitic cross capacitance 245 based on the parasitic impedance, the effective capacitances, and the voltage measurements. (Block 652). In some examples, the second parasitic capacitance determination circuitry 455 determines the parasitic cross capacitances 240 and 245 by solving Equations (19) and (20), above. In such examples, the operations of Blocks 644-652 may be referred to as cross-talk measurements.

Now turning to FIG. 6C, the first multiplexer 308 supplies the excitation current to the third electrode 160. (Block 656). In some examples, the multiplexer controller 420 controls the first multiplexer 308 to provide the first excitation current ($I_{RINT1}$) to the third impedance circuitry 314. In such examples, the third impedance circuitry 314 supplies the first excitation current to the third electrode 160.

The calibration circuitry 320 measures voltages of the calibration terminals ($V_{CAL}$) and the excitation terminals ($V_{BIA}$) of the first impedance circuitry 310, the second impedance circuitry 312, the third impedance circuitry 314, and the fourth impedance circuitry 316. (Block 660). In some examples, the second multiplexer 318 couples the excitation terminals and the calibration terminals of the impedance circuitries 310-316 to the measurement circuitry 415. In such examples, the measurement circuitry 415 may use sequencing to cause the multiplexer controller 420 to control the second multiplexer 318. In other examples, the measurement circuitry 415 may be directly coupled to the excitation terminals and the calibration terminals of the impedance circuitries 310-316.

The second parasitic capacitance determination circuitry 455 determines the sixth parasitic cross capacitance 250 based on the parasitic impedance, the effective capacitances, and the voltage measurements. (Block 664). In some examples, the second parasitic capacitance determination circuitry 455 determines the sixth parasitic cross capacitance 250 by solving Equation (21), above. In such examples, the operations of Blocks 656-664 may be referred to as crosstalk measurements.

The second parasitic capacitance determination circuitry 455 determines the first parasitic capacitance 205 of the first electrode 140 based on the parasitic cross capacitances and the effective capacitances. (Block 668). In some examples, the second parasitic capacitance determination circuitry 455 determines the first parasitic capacitance 205 by solving Equation (12), above. In such examples, the second parasitic capacitance determination circuitry 455 may use the effective capacitances from Block 628 as an approximation of the parasitic capacitances 210-220.

The second parasitic capacitance determination circuitry 455 determines the second parasitic capacitance 210 of the second electrode 150 based on the parasitic cross capacitances and the effective capacitances. (Block 672). In some examples, the second parasitic capacitance determination circuitry 455 determines the second parasitic capacitance 210 by solving Equation (13), above. In such examples, the second parasitic capacitance determination circuitry 455 may use the effective capacitances from Block 628 as an approximation of the parasitic capacitances 215 and 220.

The second parasitic capacitance determination circuitry 455 determines the third parasitic capacitance 215 of the third electrode 160 based on the parasitic cross capacitances and the effective capacitances. (Block 676). In some examples, the second parasitic capacitance determination circuitry 455 determines the third parasitic capacitance 215 by solving Equation (14), above. In such examples, the second parasitic capacitance determination circuitry 455 may use the effective capacitances from Block 628 as an approximation of the fourth parasitic capacitance 220.

The second parasitic capacitance determination circuitry 455 determines the fourth parasitic capacitance 220 of the fourth electrode 170 based on the parasitic cross capacitances 225-250 and the effective capacitances. (Block 680). In some examples, the second parasitic capacitance determination circuitry 455 determines the fourth parasitic capacitance 220 by solving Equation (15), above.

The second parasitic capacitance determination circuitry 455 re-determines the parasitic capacitances 205-220 based on the parasitic cross capacitances 225-250 and the parasitic capacitances 205-220. (Block 684). In some examples, the second parasitic capacitance determination circuitry 455 iterates through Equations (12)-(15) to re-determine using the parasitic capacitances 205-220 determined in Blocks 668-680. In such examples, the second parasitic capacitance determination circuitry 455 modifies the parasitic capacitances 205-220 as the iteration continues. For example, the second parasitic capacitance determination circuitry 455 re-determines the first parasitic capacitance 205 using the parasitic capacitances 210-220, from Blocks 672-680. In such an example, the second parasitic capacitance determination circuitry 455 re-determines the second parasitic capacitance 210 using the parasitic capacitances 215 and 220, from Blocks 676 and 680, and the re-determined value of the first parasitic capacitance 205.

The second parasitic capacitance determination circuitry 455 determines if values of the parasitic capacitances 205-220 have converged. (Block 688). In some examples, the second parasitic capacitance determination circuitry 455 determines the parasitic capacitances 205-220 are reduced after re-determining the parasitic capacitances 205-220 a plurality of times. For example, control returns to Block 684. In other examples, the second parasitic capacitance determination circuitry 455 determines that the values of the parasitic capacitances 205-220 have converged on a value if the value is approximately the same as a previous iteration.

If the second parasitic capacitance determination circuitry 455 determines the parasitic capacitances 205-220 are not reduced (e.g., Block 688 returns a result of NO), the control proceeds to return to Block 684. If the second parasitic capacitance determination circuitry 455 determines the parasitic capacitances 205-220 are reduced (e.g., Block 688 returns a result of YES), the control proceeds to end.

Although example processes are described with reference to the flowchart illustrated in FIGS. 6A, 6B, and 6C, many other methods of determining parasitic capacitances may alternatively be used in accordance with the teachings of this description. For example, the order of execution of the blocks may be changed, and/or some of the blocks described may be changed, eliminated, or combined. Similarly, additional operations may be included in the manufacturing process before, in between, or after the blocks shown in the illustrated examples.

As used herein, "processor circuitry" is defined to include (i) one or more special purpose electrical circuits structured to perform specific operation(s) and including one or more semiconductor-based logic devices (e.g., electrical hardware implemented by one or more transistors), and/or (ii) one or more general purpose semiconductor-based electrical circuits programmable with instructions to perform specific operations and including one or more semiconductor-based logic devices (e.g., electrical hardware implemented by one or more transistors). Examples of processor circuitry include programmable microprocessors, Field Programmable Gate Arrays (FPGAs) that may instantiate instructions, Central Processor Units (CPUs), Graphics Processor Units (GPUs), Digital Signal Processors (DSPs), XPUs, or microcontrollers and integrated circuits such as Application Specific Integrated Circuits (ASICs). For example, an XPU may be implemented by a heterogeneous computing system including multiple types of processor circuitry (e.g., one or more FPGAs, one or more CPUs, one or more GPUs, one or more DSPs, etc., and/or a combination thereof) and application programming interface(s) (API(s)) that may assign computing task(s) to whichever one(s) of the multiple types of processor circuitry is/are best suited to execute the computing task(s).

Figure 7:
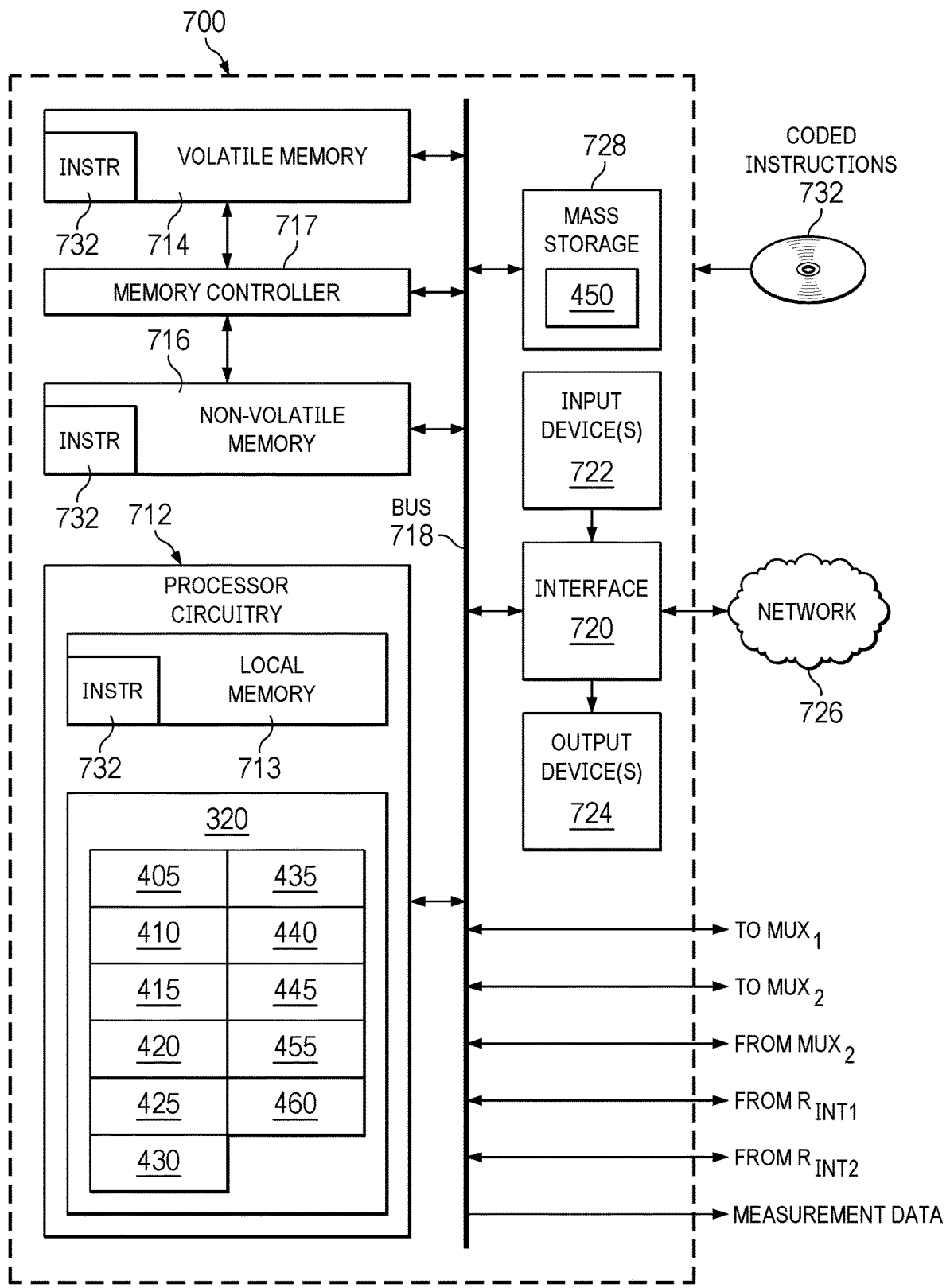
FIG. 7 is a block diagram of an example processing platform including processor circuitry structured to execute the example machine readable instructions and/or the example operations of FIGS. 5A-6C to implement the calibration circuitry of FIGS. 3 and 4.

FIG. 7 is a block diagram of an example processor platform 700 structured to execute and/or instantiate the machine-readable instructions and/or the operations of FIGS. 5A-6C to implement the calibration circuitry 320 of FIGS. 3 and 4. The processor platform 700 can be, for example, a server, a personal computer, a workstation, a self-learning machine (e.g., a neural network), a mobile device (e.g., a cell phone, a smart phone, a tablet such as an iPad™), a personal digital assistant (PDA), a headset (e.g., an augmented reality (AR) headset, a virtual reality (VR) headset, etc.) or other wearable device, or any other type of computing device.

The processor platform 700 of the illustrated example includes processor circuitry 712. The processor circuitry 712 of the illustrated example is hardware. For example, the processor circuitry 712 can be implemented by one or more integrated circuits, logic circuits, FPGAs, microprocessors, CPUs, GPUs, DSPs, and/or microcontrollers from any desired family or manufacturer. The processor circuitry 712 may be implemented by one or more semiconductor based (e.g., silicon based) devices. In this example, the processor circuitry 712 implements the circuitries 405-445, 455, and 460 of FIG. 4.

The processor circuitry 712 of the illustrated example includes a local memory 713 (e.g., a cache, registers, etc.). The processor circuitry 712 of the illustrated example is in communication with a main memory including a volatile memory 714 and a non-volatile memory 716 by a bus 718. The volatile memory 714 may be implemented by Synchronous Dynamic Random Access Memory (SDRAM), Dynamic Random Access Memory (DRAM), RAMBUS® Dynamic Random Access Memory (RDRAM®), and/or any other type of RAM device. The non-volatile memory 716 may be implemented by flash memory and/or any other desired type of memory device. Access to the main memory 714, 716 of the illustrated example is controlled by a memory controller 717.

The processor platform 700 of the illustrated example also includes interface circuitry 720. The interface circuitry 720 may be implemented by hardware in accordance with any type of interface standard, such as an Ethernet interface, a universal serial bus (USB) interface, a Bluetooth® interface, a near field communication (NFC) interface, a Peripheral Component Interconnect (PCI) interface, and/or a Peripheral Component Interconnect Express (PCIe) interface.

In the illustrated example, one or more input devices 722 are connected to the interface circuitry 720. The input device(s) 722 permit(s) a user to enter data and/or commands into the processor circuitry 712. The input device(s) 722 can be implemented by, for example, an audio sensor, a microphone, a camera (still or video), a keyboard, a button, a mouse, a touchscreen, an isopoint device, and/or a voice recognition system.

One or more output devices 724 are also connected to the interface circuitry 720 of the illustrated example. The output device(s) 724 can be implemented, for example, by display devices (e.g., a light emitting diode (LED), an organic light emitting diode (OLED), a liquid crystal display (LCD), a cathode ray tube (CRT) display, an in-place switching (IPS) display, a touchscreen, etc.), a tactile output device, a printer, and/or speaker. The interface circuitry 720 of the illustrated example, thus, typically includes a graphics driver card, a graphics driver chip, and/or graphics processor circuitry such as a GPU.

The interface circuitry 720 of the illustrated example also includes a communication device such as a transmitter, a receiver, a transceiver, a modem, a residential gateway, a wireless access point, and/or a network interface to facilitate exchange of data with external machines (e.g., computing devices of any kind) by a network 726. The communication can be by, for example, an Ethernet connection, a digital subscriber line (DSL) connection, a telephone line connection, a coaxial cable system, a satellite system, a line-of-site wireless system, a cellular telephone system, an optical connection, etc.

The processor platform 700 of the illustrated example also includes one or more mass storage devices 728 to store software and/or data. Examples of such mass storage devices 728 include magnetic storage devices, optical storage devices, floppy disk drives, HDDs, CDs, Blu-ray disk drives, redundant array of independent disks (RAID) systems, solid state storage devices such as flash memory devices and/or SSDs, and DVD drives.

The machine-readable instructions 732, which may be implemented by the machine readable instructions of FIGS. 5A-6C, may be stored in the mass storage device 728, in the volatile memory 714, in the non-volatile memory 716, and/or on a removable non-transitory computer readable storage medium such as a CD or DVD.

Figure 8:
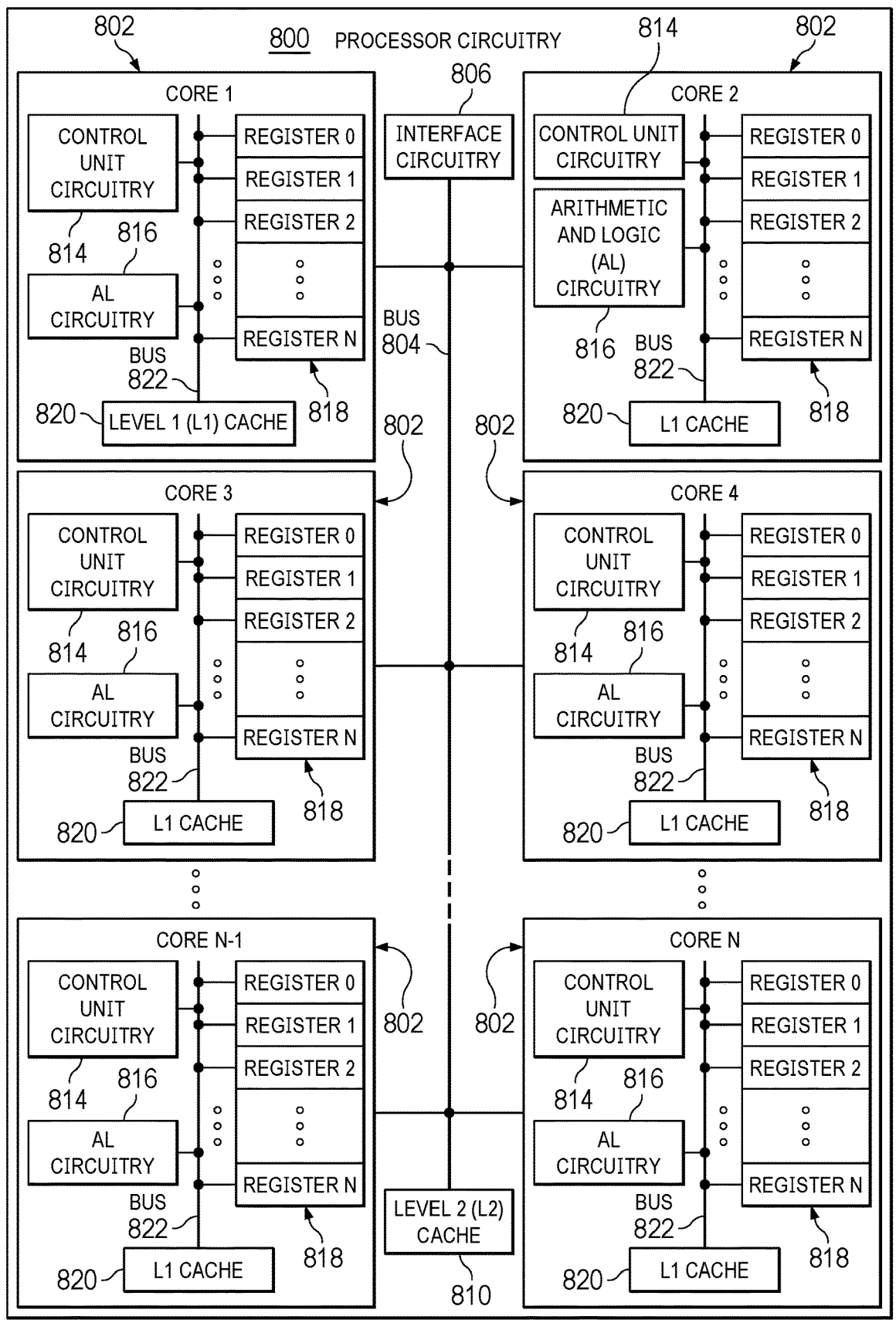
FIG. 8 is a block diagram of an example implementation of the processor circuitry of FIG. 7.

FIG. 8 is a block diagram of an example implementation of the processor circuitry 712 of FIG. 7. In this example, the processor circuitry 712 of FIG. 7 is implemented by a microprocessor 800. For example, the microprocessor 800 may be a general purpose microprocessor (e.g., general purpose microprocessor circuitry). The microprocessor 800 executes some or all of the machine readable instructions of the flowcharts of FIGS. 5A-6C to effectively instantiate the calibration circuitry 320 of FIGS. 3 and 4 as logic circuits to perform the operations corresponding to those machine readable instructions. In some such examples, the calibration circuitry 320 of FIGS. 3 and 4 is instantiated by the hardware circuits of the microprocessor 800 in combination with the instructions. For example, the microprocessor 800 may be implemented by multi-core hardware circuitry such as a CPU, a DSP, a GPU, an XPU, etc. Although it may include any number of example cores 802 (e.g., 1 core), the microprocessor 800 of this example is a multi-core semiconductor device including N cores. The cores 802 of the microprocessor 800 may operate independently or may cooperate to execute machine readable instructions. For example, machine code corresponding to a firmware program, an embedded software program, or a software program may be executed by one of the cores 802 or may be executed by multiple ones of the cores 802 at the same or different times. In some examples, the machine code corresponding to the firmware program, the embedded software program, or the software program is split into threads and executed in parallel by two or more of the cores 802. The software program may correspond to a portion or all of the machine readable instructions and/or operations represented by the flowcharts of FIGS. 5A-6C.

The cores 802 may communicate by a first example bus 804. In some examples, the first bus 804 may be implemented by a communication bus to effectuate communication associated with one(s) of the cores 802. For example, the first bus 804 may be implemented by at least one of an Inter-Integrated Circuit (I2C) bus, a Serial Peripheral Interface (SPI) bus, a PCI bus, or a PCIe bus. Additionally or alternatively, the first bus 804 may be implemented by any other type of computing or electrical bus. The cores 802 may obtain data, instructions, and/or signals from one or more external devices by example interface circuitry 806. The cores 802 may output data, instructions, and/or signals to the one or more external devices by the interface circuitry 806. Although the cores 802 of this example include example local memory 820 (e.g., Level 1 (L1) cache that may be split into an L1 data cache and an L1 instruction cache), the microprocessor 800 also includes example shared memory 810 that may be shared by the cores (e.g., Level 2 (L2 cache)) for high-speed access to data and/or instructions. Data and/or instructions may be transferred (e.g., shared) by writing to and/or reading from the shared memory 810. The local memory 820 of each of the cores 802 and the shared memory 810 may be part of a hierarchy of storage devices including multiple levels of cache memory and the main memory (e.g., the main memory 714, 716 of FIG. 7). Typically, higher levels of memory in the hierarchy exhibit lower access time and have smaller storage capacity than lower levels of memory. Changes in the various levels of the cache hierarchy are managed (e.g., coordinated) by a cache coherency policy.

Each core 802 may be referred to as a CPU, DSP, GPU, etc., or any other type of hardware circuitry. Each core 802 includes control unit circuitry 814, arithmetic and logic (AL) circuitry (sometimes referred to as an ALU) 816, a plurality of registers 818, the local memory 820, and a second example bus 822. Other structures may be present. For example, each core 802 may include vector unit circuitry, single instruction multiple data (SIMD) unit circuitry, load/store unit (LSU) circuitry, branch/jump unit circuitry, floating-point unit (FPU) circuitry, etc. The control unit circuitry 814 includes semiconductor-based circuits structured to control (e.g., coordinate) data movement within the corresponding core 802. The AL circuitry 816 includes semiconductor-based circuits structured to perform one or more mathematic and/or logic operations on the data within the corresponding core 802. The AL circuitry 816 of some examples performs integer based operations. In other examples, the AL circuitry 816 also performs floating point operations. In yet other examples, the AL circuitry 816 may include first AL circuitry that performs integer based operations and second AL circuitry that performs floating point operations. In some examples, the AL circuitry 816 may be referred to as an Arithmetic Logic Unit (ALU). The registers 818 are semiconductor-based structures to store data and/or instructions such as results of one or more of the operations performed by the AL circuitry 816 of the corresponding core 802. For example, the registers 818 may include vector register(s), SIMD register(s), general purpose register(s), flag register(s), segment register(s), machine specific register(s), instruction pointer register(s), control register(s), debug register(s), memory management register(s), machine check register(s), etc. The registers 818 may be arranged in a bank as shown in FIG. 8. Alternatively, the registers 818 may be organized in any other arrangement, format, or structure including distributed throughout the core 802 to shorten access time. The second bus 822 may be implemented by at least one of an I2C bus, a SPI bus, a PCI bus, or a PCIe bus.

Figure 9:
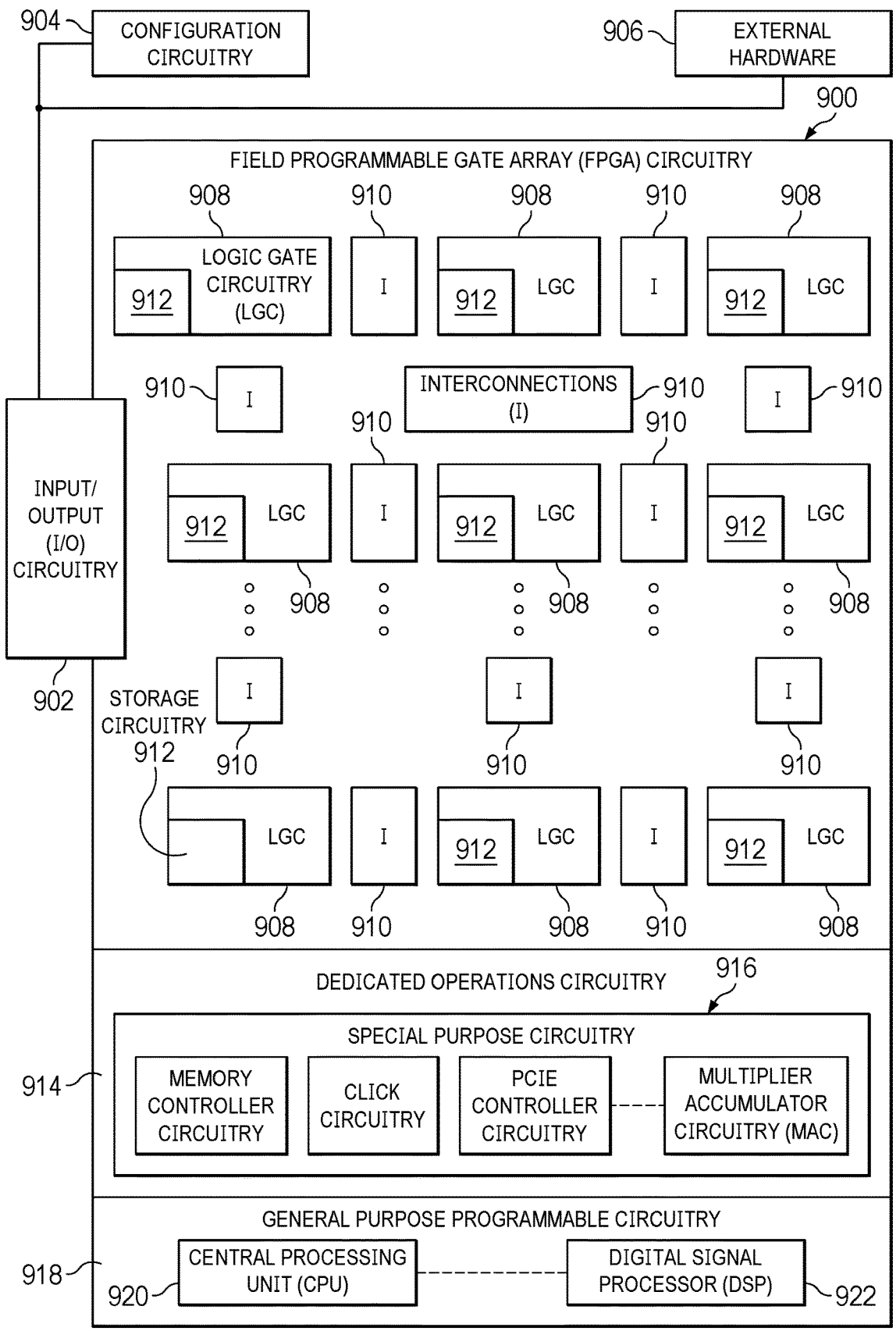
FIG. 9 is a block diagram of another example implementation of the processor circuitry of FIG. 7.

Each core 802 and/or, more generally, the microprocessor 800 may include additional and/or alternate structures to those shown and described above. For example, one or more clock circuits, one or more power supplies, one or more power gates, one or more cache home agents (CHAs), one or more converged/common mesh stops (CMS s), one or more shifters (e.g., barrel shifter(s)) and/or other circuitry may be present. The microprocessor 800 is a semiconductor device fabricated to include many transistors interconnected to implement the structures described above in one or more integrated circuits (ICs) contained in one or more packages. The processor circuitry may include and/or cooperate with one or more accelerators. In some examples, accelerators are implemented by logic circuitry to perform certain tasks more quickly and/or efficiently than can be done by a general purpose processor. Examples of accelerators include ASICs and FPGAs such as those described herein. A GPU or other programmable device can also be an accelerator. Accelerators may be on-board the processor circuitry, in the same chip package as the processor circuitry and/or in one or more separate packages from the processor circuitry.

FIG. 9 is a block diagram of another example implementation of the processor circuitry 712 of FIG. 7. In this example, the processor circuitry 712 is implemented by FPGA circuitry 900. For example, the FPGA circuitry 900 may be implemented by an FPGA. The FPGA circuitry 900 can be used, for example, to perform operations that could otherwise be performed by the example microprocessor 800 of FIG. 8 executing corresponding machine-readable instructions. However, once configured, the FPGA circuitry 900 instantiates the machine-readable instructions in hardware and, thus, can often execute the operations faster than they could be performed by a general purpose microprocessor executing the corresponding software.

More specifically, in contrast to the microprocessor 800 of FIG. 8 described above (which is a general purpose device that may be programmed to execute some or all of the machine readable instructions represented by the flowcharts of FIG. 5A-6C but whose interconnections and logic circuitry are fixed once fabricated), the FPGA circuitry 900 of the example of FIG. 9 includes interconnections and logic circuitry that may be configured and/or interconnected in different ways after fabrication to instantiate, for example, some or all of the machine readable instructions represented by the flowcharts of FIGS. 5A-6C. In particular, the FPGA circuitry 900 may be thought of as an array of logic gates, interconnections, and switches. The switches can be programmed to change how the logic gates are interconnected by the interconnections, effectively forming one or more dedicated logic circuits (unless and until the FPGA circuitry 900 is reprogrammed). The configured logic circuits enable the logic gates to cooperate in different ways to perform different operations on data received by input circuitry. Those operations may correspond to some or all of the software represented by the flowcharts of FIGS. 5A-6C. As such, the FPGA circuitry 900 may be structured to effectively instantiate some or all of the machine-readable instructions of the flowcharts of FIGS. 5A-6C as dedicated logic circuits to perform the operations corresponding to those software instructions in a dedicated manner analogous to an ASIC. Therefore, the FPGA circuitry 900 may perform the operations corresponding to the some or all of the machine-readable instructions of FIGS. 5A-6C faster than the general purpose microprocessor can execute the same.

In the example of FIG. 9, the FPGA circuitry 900 is structured to be programmed (and/or reprogrammed one or more times) by an end user by a hardware description language (HDL) such as Verilog. The FPGA circuitry 900 of FIG. 9, includes example input/output (I/O) circuitry 902 to obtain and/or output data to/from example configuration circuitry 904 and/or external hardware 906. For example, the configuration circuitry 904 may be implemented by interface circuitry that may obtain machine readable instructions to configure the FPGA circuitry 900, or portion(s) thereof. In some such examples, the configuration circuitry 904 may obtain the machine readable instructions from a user, a machine (e.g., hardware circuitry (e.g., programmed or dedicated circuitry) that may implement an Artificial Intelligence/Machine Learning (AI/ML) model to generate the instructions), etc. In some examples, the external hardware 906 may be implemented by external hardware circuitry. For example, the external hardware 906 may be implemented by the microprocessor 800 of FIG. 8. The FPGA circuitry 900 also includes an array of example logic gate circuitry 908, a plurality of example configurable interconnections 910, and example storage circuitry 912. The logic gate circuitry 908 and the configurable interconnections 910 are configurable to instantiate one or more operations that may correspond to at least some of the machine-readable instructions of FIGS. 5A-6C and/or other desired operations. The logic gate circuitry 908 shown in FIG. 9 is fabricated in groups or blocks. Each block includes semiconductor-based electrical structures that may be configured into logic circuits. In some examples, the electrical structures include logic gates (e.g., And gates, Or gates, Nor gates, etc.) that provide basic building blocks for logic circuits. Electrically controllable switches (e.g., transistors) are present within each of the logic gate circuitry 908 to enable configuration of the electrical structures and/or the logic gates to form circuits to perform desired operations. The logic gate circuitry 908 may include other electrical structures such as look-up tables (LUTs), registers (e.g., flip-flops or latches), multiplexers, etc.

The configurable interconnections 910 of the illustrated example are conductive pathways, traces, vias, or the like that may include electrically controllable switches (e.g., transistors) whose state can be changed by programming (e.g., using an HDL instruction language) to activate or deactivate one or more connections between one or more of the logic gate circuitry 908 to program desired logic circuits.

The storage circuitry 912 of the illustrated example is structured to store result(s) of the one or more of the operations performed by corresponding logic gates. The storage circuitry 912 may be implemented by registers or the like. In the illustrated example, the storage circuitry 912 is distributed amongst the logic gate circuitry 908 to facilitate access and increase execution speed.

The example FPGA circuitry 900 of FIG. 9 also includes example Dedicated Operations Circuitry 914. In this example, the Dedicated Operations Circuitry 914 includes special purpose circuitry 916 that may be invoked to implement commonly used functions to avoid the need to program those functions in the field. Examples of such special purpose circuitry 916 include memory (e.g., DRAM) controller circuitry, PCIe controller circuitry, clock circuitry, transceiver circuitry, memory, and multiplier-accumulator circuitry. Other types of special purpose circuitry may be present. In some examples, the FPGA circuitry 900 may also include example general purpose programmable circuitry 918 such as an example CPU 920 and/or an example DSP 922. Other general purpose programmable circuitry 918 may additionally or alternatively be present such as a GPU, an XPU, etc., that can be programmed to perform other operations.

Although FIGS. 8 and 9 illustrate two example implementations of the processor circuitry 712 of FIG. 7, many other approaches are contemplated. For example, as mentioned above, modern FPGA circuitry may include an on-board CPU, such as one or more of the example CPU 920 of FIG. 9. Therefore, the processor circuitry 712 of FIG. 7 may additionally be implemented by combining the example microprocessor 800 of FIG. 8 and the example FPGA circuitry 900 of FIG. 9. In some such hybrid examples, a first portion of the machine readable instructions represented by the flowcharts of FIGS. 5A-6C may be executed by one or more of the cores 802 of FIG. 8, a second portion of the machine readable instructions represented by the flowcharts of FIGS. 5A-6C may be executed by the FPGA circuitry 900 of FIG. 9, and/or a third portion of the machine readable instructions represented by the flowcharts of FIGS. 5A-6C may be executed by an ASIC. It should be understood that some or all of the calibration circuitry 320 of FIGS. 3 and 4 may, thus, be instantiated at the same or different times.

Some or all of the circuitry may be instantiated, for example, in one or more threads executing concurrently and/or in series. Moreover, in some examples, some or all of the calibration circuitry 320 of FIGS. 3 and 4 may be implemented within one or more virtual machines and/or containers executing on the microprocessor.

In some examples, the processor circuitry 712 of FIG. 7 may be in one or more packages. For example, the microprocessor 800 of FIG. 8 and/or the FPGA circuitry 900 of FIG. 9 may be in one or more packages. In some examples, an XPU may be implemented by the processor circuitry 712 of FIG. 7, which may be in one or more packages. For example, the XPU may include a CPU in one package, a DSP in another package, a GPU in yet another package, and an FPGA in still yet another package.

In this description, the term "and/or" (when used in a form such as A, B and/or C) refers to any combination or subset of A, B, C, such as: (a) A alone; (b) B alone; (c) C alone; (d) A with B; (e) A with C; (f) B with C; and (g) A with B and with C. Also, as used herein, the phrase "at least one of A or B" (or "at least one of A and B") refers to implementations including any of: (a) at least one A; (b) at least one B; and (c) at least one A and at least one B.

The term "couple" is used throughout the specification. The term may cover connections, communications, or signal paths that enable a functional relationship consistent with this description. For example, if device A provides a signal to control device B to perform an action, in a first example device A is coupled to device B, or in a second example device A is coupled to device B through intervening component C if intervening component C does not substantially alter the functional relationship between device A and device B such that device B is controlled by device A via the control signal provided by device A.

Numerical identifiers such as "first", "second", "third", etc. are used merely to distinguish between elements of substantially the same type in terms of structure and/or function. These identifiers as used in the detailed description do not necessarily align with those used in the claims.

A device that is "configured to" perform a task or function may be configured (e.g., programmed and/or hardwired) at a time of manufacturing by a manufacturer to perform the function and/or may be configurable (or re-configurable) by a user after manufacturing to perform the function and/or other additional or alternative functions. The configuring may be through firmware and/or software programming of the device, through a construction and/or layout of hardware components and interconnections of the device, or a combination thereof.

As used herein, the terms "terminal", "node", "interconnection", "pin" and "lead" are used interchangeably. Unless specifically stated to the contrary, these terms are generally used to mean an interconnection between or a terminus of a device element, a circuit element, an integrated circuit, a device or other electronics or semiconductor component.

A circuit or device that is described herein as including certain components may instead be adapted to be coupled to those components to form the described circuitry or device. For example, a structure described as including one or more semiconductor elements (such as transistors), one or more passive elements (such as resistors, capacitors, and/or inductors), and/or one or more sources (such as voltage and/or current sources) may instead include only the semiconductor elements within a single physical device (e.g., a semiconductor die and/or integrated circuit (IC) package) and may be adapted to be coupled to at least some of the passive elements and/or the sources to form the described structure either at a time of manufacture or after a time of manufacture, for example, by an end-user and/or a third-party.

Circuits described herein are reconfigurable to include the replaced components to provide functionality at least partially similar to functionality available prior to the component replacement. Components shown as resistors, unless otherwise stated, are generally representative of any one or more elements coupled in series and/or parallel to provide an amount of impedance represented by the shown resistor. For example, a resistor or capacitor shown and described herein as a single component may instead be multiple resistors or capacitors, respectively, coupled in parallel between the same nodes. For example, a resistor or capacitor shown and described herein as a single component may instead be multiple resistors or capacitors, respectively, coupled in series between the same two nodes as the single resistor or capacitor. While certain elements of the described examples are included in an integrated circuit and other elements are external to the integrated circuit, in other examples, additional or fewer features may be incorporated into the integrated circuit. In addition, some or all of the features illustrated as being external to the integrated circuit may be included in the integrated circuit and/or some features illustrated as being internal to the integrated circuit may be incorporated outside of the integrated. As used herein, the term "integrated circuit" means one or more circuits that are: (i) incorporated in/over a semiconductor substrate; (ii) incorporated in a single semiconductor package; (iii) incorporated into the same module; and/or (iv) incorporated in/on the same printed circuit board.

Uses of the phrase "ground" in the foregoing description include a chassis ground, an Earth ground, a floating ground, a virtual ground, a digital ground, a common ground, and/or any other form of ground connection applicable to, or suitable for, the teachings of this description. Unless otherwise stated, "about," "approximately," or "substantially" preceding a value means +/−10 percent of the stated value, or, if the value is zero, a reasonable range of values around zero.

Modifications are possible in the described examples, and other examples are possible, within the scope of the claims.

What is claimed is:

1. An apparatus comprising:
   first impedance circuitry including:
      a first impedance circuit having a first terminal, a second terminal, and a first impedance value;
      a second impedance circuit having a first terminal, a second terminal, and a second impedance value, the first terminal of the second impedance circuit coupled to the second terminal of the first impedance circuit; and
      a third impedance circuit having a first terminal, a second terminal, and a third impedance value, the first terminal of the third impedance circuit coupled to the second terminal of the first impedance circuit;
   second impedance circuitry including:
      a fourth impedance circuit having a first terminal, a second terminal, and the first impedance value;
      a fifth impedance circuit having a first terminal, a second terminal, and the second impedance value, the first terminal of the fifth impedance circuit coupled to the second terminal of the fourth impedance circuit; and
      a sixth impedance circuit having a first terminal, a second terminal, and the third impedance value, the first terminal of the sixth impedance circuit coupled to the second terminal of the fourth impedance circuit; and calibration circuitry coupled to the first impedance circuitry and the second impedance circuitry.

2. The apparatus of claim 1, further including:

a transmitter including a first terminal; and a multiplexer including an input, a first output, and a second output, the input of the multiplexer coupled to the first terminal of the transmitter, the first output coupled to the first terminal of the first impedance circuit, the second output of the multiplexer coupled to the first terminal of the fourth impedance circuit.

3. The apparatus of claim 1, further including:

a first electrode coupled to the second terminal of the second impedance circuit; and a second electrode coupled to the second terminal of the fifth impedance circuit.

4. A system comprising:

a first electrode having a first terminal;

a second electrode having a first terminal; and measurement circuitry coupled to the first electrode and the second electrode, the measurement circuitry including:
- first impedance circuitry having a first terminal, a second terminal and a third terminal, the second terminal of the first impedance circuitry coupled to the first terminal of the first electrode;
- second impedance circuitry having a first terminal, a second terminal and a third terminal, the second terminal of the second impedance circuitry coupled to the first terminal of the second electrode;
- calibration circuitry coupled to the first terminal and the second terminal of the first impedance circuitry and the first terminal and the second terminal of the second impedance circuitry.

5. The system of claim 4, wherein the measurement circuitry further including:

a transmitter including a first terminal; and a multiplexer including an input, a first output, and a second output, the input of the multiplexer coupled to the first terminal of the transmitter, the first output coupled to the first terminal of the first impedance circuitry, the second output of the multiplexer coupled to the first terminal of the second impedance circuitry.

6. The system of claim 4, wherein the first impedance circuitry further having a fourth terminal, the first impedance circuitry including:

a first impedance circuit coupled between the first terminal and the fourth terminal of the first impedance circuitry;

a second impedance circuit coupled between the second terminal and the fourth terminal of the first impedance circuitry; and a third impedance circuit coupled between the third terminal and the fourth terminal of the first impedance circuitry.

7. An apparatus comprising:

a transmitter configured to generate an excitation signal, the excitation signal having an excitation current;

first impedance circuitry having a first terminal, a second terminal, a third terminal, a first impedance value, a second impedance value, and a third impedance value;

second impedance circuitry having a first terminal, a second terminal, a third terminal, the first impedance value, the second impedance value, and the third impedance value;

a multiplexer having a control input, the control input configured to cause the multiplexer to provide the excitation signal to one of the first impedance circuitry or the second impedance circuitry;

calibration circuitry coupled to the first impedance circuitry, the second impedance circuitry, and the multiplexer.

* * * * *